(12) United States Patent
Hossain et al.

(10) Patent No.: US 10,161,874 B2
(45) Date of Patent: *Dec. 25, 2018

(54) POLARIZATION DEPENDENT SURFACE ENHANCED RAMAN SCATTERING SYSTEM

(71) Applicant: King Fahd University of Petroleum and Minerals, Dhahran (SA)

(72) Inventors: Mohammad Kamal Hossain, Dhahran (SA); Yukihiro Ozaki, Dhahran (SA)

(73) Assignee: King Fahd University of Petroleum and Minerals, Dhahran (SA)

( * ) Notice: Subject to any disclaimer, the term of this patent is extended or adjusted under 35 U.S.C. 154(b) by 0 days.

This patent is subject to a terminal disclaimer.

(21) Appl. No.: 15/976,967

(22) Filed: May 11, 2018

(65) Prior Publication Data

US 2018/0284029 A1    Oct. 4, 2018

Related U.S. Application Data

(63) Continuation of application No. 15/682,847, filed on Aug. 22, 2017, now Pat. No. 9,995,687, which is a (Continued)

(51) Int. Cl.
  *G01N 21/65* (2006.01)
  *B81C 1/00* (2006.01)
  *B82B 1/00* (2006.01)

(52) U.S. Cl.
  CPC ....... *G01N 21/658* (2013.01); *B81C 1/00849* (2013.01); *B82B 1/00* (2013.01)

(58) Field of Classification Search
  CPC .. G01N 21/658; G01N 2021/651; B05D 1/18; B08B 3/04

(Continued)

(56) References Cited

U.S. PATENT DOCUMENTS

| 5,864,397 A | 1/1999 | Vo-Dinh |
| 9,772,290 B2 | 9/2017 | Hossain |

(Continued)

FOREIGN PATENT DOCUMENTS

| CN | 102828176 A | 12/2012 |
| WO | 2014/121134 A2 | 8/2014 |

OTHER PUBLICATIONS

Liu, X., et al., "Ordered gold nanoparticle arrays as surface-enhanced Raman spectroscopy substrates for label-free detection of nitroexplosives", TALANTA, vol. 83, pp. 1023-1029, (2011).

*Primary Examiner* — Hina F Ayub
(74) *Attorney, Agent, or Firm* — Oblon, McClelland, Maier & Neustadt, L.L.P.

(57) ABSTRACT

A surface enhanced Raman scattering (SERS) active nanoassembly comprising anisotropically assembled gold nanoparticles in a monolayer double row immobilized on a glass layer is disclosed. The discrete gold nanoparticles are separated by interparticle gaps of 0.5-10 nm that provide hotsites where appropriate excitation creates surface plasmon resonaces and regions of strong and localized electromagnetic fields that enhance Raman signal substantially, $10^4$-$10^{15}$ fold. An appropriate SERS apparatus comprising the nanoassembly for detecting an analyte is also disclosed. In addition, a method for producing the nanoassembly as well as the application of the nanoassembly or the apparatus comprising the nanoassembly in a method for measuring the SERS signal of an analyte is disclosed.

3 Claims, 13 Drawing Sheets

Related U.S. Application Data continuation of application No. 14/921,442, filed on Oct. 23, 2015, now Pat. No. 9,772,290.

(58) Field of Classification Search
USPC .......................................................... 356/301
See application file for complete search history.

(56) References Cited

U.S. PATENT DOCUMENTS

| | | |
|---|---|---|
| 2002/0123050 A1 | 9/2002 | Poponin |
| 2004/0142484 A1 | 7/2004 | Berlin |
| 2005/0003376 A1 | 1/2005 | Kneipp et al. |
| 2008/0064788 A1 | 3/2008 | Ben-Moshe |
| 2008/0135091 A1 | 6/2008 | Cheng |
| 2008/0305489 A1 | 12/2008 | Thomas |
| 2010/0245814 A1 | 9/2010 | Jablonski |
| 2011/0128536 A1 | 6/2011 | Bond |
| 2011/0166045 A1 | 7/2011 | Dhawan |
| 2011/0267613 A1 | 11/2011 | Amako |
| 2011/0311822 A1 | 12/2011 | Hao |
| 2012/0064134 A1 | 3/2012 | Bourke, Jr. |
| 2014/0354993 A1 | 12/2014 | Lin |
| 2015/0116706 A1 | 4/2015 | Barcelo |
| 2016/0018335 A1 | 1/2016 | Xiong |
| 2016/0252459 A1 | 9/2016 | Bell |

POLARIZATION DEPENDENT SURFACE ENHANCED RAMAN SCATTERING SYSTEM

CROSS-REFERENCE TO RELATED APPLICATIONS

The present application is a Continuation of Ser. No. 15/682,847, now allowed, having a filing date of Aug. 22, 2017 which is a Continuation of Ser. No. 14/921,442, now U.S. Pat. No. 9,772,290, having a filing date of Oct. 23, 2015.

BACKGROUND OF THE INVENTION

Technical Field

The present disclosure relates to an anisotropic surface enhanced Raman scattering (SERS) nanoassembly of gold nanoparticles. The present disclosure further relates to an apparatus comprising the nanoassembly for detecting an analyte. Additionally, the present disclosure relates to a method for producing the nanoassembly as well as its application in a method for measuring the SERS signal of an analyte.

Description of the Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

Surface enhanced Raman scattering (SERS) has become a center of interest in recent science and technology [Y. Kitahama, M. K. Hossain and Y. Ozaki, *Raman, Infrared, and Near-infrared Chemical Imaging* (Ed: S. Sasic, Y. Ozaki), John Wiley and Sons, Inc., Hoboken, N.J., 2010.; and R. A. Halvorson and P. J. Vikesland, *Environ. Sci. Tech.,* 2010, 44, 7749-7755.; and M. K. Hossain and Y. Ozaki, *Curr. Sci.,* 2009, 97, 192-201.; and Y. Ozaki, K. Kneipp and R. Aroca, *Frontiers of surface-enhanced Raman scattering*; John Wiley & Sons Ltd., Chichester, 2014.; and E. C. Le Ru and P. G. Etchegoin, *Principles of surface-enhanced Raman spectroscopy and related plasmonic effects*, Elsevier, Amsterdam, 2009.; and K. Kneipp, M. Moskovits and H. Kneipp, *Surface Enhanced Raman Scattering—Physics and applications*, Springer, Heidelberg and Berlin, 2006.; and R. Aroca, *Surface-Enhanced Vibrational Spectroscopy*, John Wiley & Sons Ltd., Chichester, 2006.—each incorporated herein by reference in its entirety]. SERS is not only simple with single molecule detection capability but also inherits the fine molecular specificity from the Raman effect of the analyte of interest [M. K. Hossain, Y. Kitahama, G. Huang, X. Han and Y. Ozaki, *Anal. Bioanal. Chem.,* 2009, 394, 1747-1761.; and S. Schlucker, *Angew. Chem. Int. Ed.,* 2014, 53, 4756-95.; and K. A. Willets, *Chem. Soc. Rev.,* 2014, 43, 3854-3864.; and M. K. Hossain, *Mater. Sci. forum,* 2013, 754, 143-169.; and P. L. Stiles, J. A. Dieringer, N. C. Shah, R. P. VanDuyne, *Annu. Rev. Anal. Chem.,* 2008, 1, 601-626.; and G. Mcnay, D. Eustace, W. E. Smith, K. Faulds and D. Graham, *Appl. Specs.,* 2011, 65, 825-837.; and H. A. Atwater, *Sci. Am.,* 2007, 296, 56-62.; and M. K. Hossain, G. R. Willmott, P. E. Etchegoin, R. Blaikie and J. R. Tallon, *Nanoscale,* 2013, 5, 8945-50.; and P. G. Etchegoin and E. C. Le Ru, *Surface Enhanced Raman Spectroscopy* (Ed.: S. Schlucker), Wiley-VCH, Weinheim, 2011.; and S. E. J Bell and A. Stewart, *Surface Enhanced Raman Spectroscopy* (Ed.: S. Schlucker), Wiley-VCH, Weinheim, 2011.; and K. A. Willets and R. P. VanDuyne, *Annu. Rev. Phys. Chem.,* 2007, 58, 267-297.—each incorporated herein by reference in its entirety]. Since SERS demands the presence of a metallic nanostructure, the phenomenon results not only from light-molecule interactions but also from light-metal interactions. The main causative factor of dramatic SERS enhancements is now known: "the analyte" must be at "the hotsite", which is the region of strong and localized electromagnetic (EM) field modulated by the analyte through its absorption and orientation. Two mechanisms are implicated in the SERS effect: EM and charge transfer (CT). It is widely accepted that the EM mechanism is more important, where surface plasmon resonances (SPRs) are induced at the interface or curvature by incident photons, causing an enormous increase in the EM field. The Raman signal of an analyte under such conditions will be enhanced by several orders of magnitude, typically $10^6$-$10^{10}$ fold. Noble metal nanoparticles, particularly unit dimers with a small interparticle gap, show a sharp plasmon excitation mediated EM field, leading to large signal enhancement, which facilitates single molecule detection in SERS [S. Nie and S. R. Emory, *Science,* 1997, 275, 1102-1106.; and K. Imura, H. Okamoto, M. K. Hossain and M. Kitajima, *Nano Lett.,* 2006, 6, 2173-2176.; and G. Haran, *Acc. Chem. Res.,* 2010, 43, 1135-1143—each incorporated herein by reference in its entirety]. Interestingly, such an EM field enhancement is strongly dependent on the incident polarization, where in-plane polarization to the interparticle axis induces the strongest enhancement [E. C. Le Ru, M. Meyer, E. Balackie and P. G. Etchegoin, *J. Raman Spectros.,* 2008, 39, 1127-1134.; and P. G. Etchegoin, C. Galloway and E. C. Le Ru, *Phys. Chem. Chem. Phys.,* 2006, 8, 2624-2628.; and E. C. Le Ru and P. G. Etchegoin, *MRS Bull.,* 2013, 38, 631-640.; and W. R. C. Somerville, B. Auguie and E. C. Le Ru, *J. Quant. Spectros. & Radia. Trans.,* 2013, 123, 153-168.; and E. C. Le Ru, L. Schroeter and P. G. Etchegoin, *Anal. Chem.,* 2012, 84, 5074-5079.—each incorporated herein by reference in its entirety]. Rigorous theoretical studies as well as some experimental studies have been undertaken to verify the mechanism underlying such an enhancement [F. J. Garcia-Vidal and J. B. Pendry, *Phys. Rev. Lett.,* 1996, 77, 1163-1166.; and H. Xu and M. Kall, *ChemPhyChem,* 2003, 4, 1001-1005.—each incorporated herein by reference in its entirety]. The polarization dependence of SERS has been investigated using silver dimers, nanorods, and coupled nanowires [M. Suzuki, W. Maekita, Y. Wada, K. Kitajima, K. Kimura, T. Fukuoka and Y. Mori, *App. Phys. Lett.,* 2006, 88, 203121-1-203121-3.; and A. R. Tao and P. Yang, *J. Phys. Chem. B,* 2005, 109, 15687-15690.; and A. G. Brolo, E. Arctander and C. J. Addison, *J. Phys. Chem. B,* 2005, 109, 401-405.—each incorporated herein by reference in its entirety]. The results of these investigations may throw light on the fundamental aspects of SERS mechanism(s) as well as analyte-metal interactions. However, most of the SERS studies have been performed using an ensemble system, where hotsites are not isolated but interact with each other and thus lose their inherent characteristics.

In ensemble SERS measurements, contrary to a single hotsite, many interstitials participate in SERS enhancement along with their wide variety of plasmon excitations [M. K. Hossain, Y. Kitahama, V. P. Biju, T. Kaneko, T. Itoh and Y. Ozaki, *J. Phys. Chem. C,* 2009, 113, 11689-11694.—incorporated herein by reference in its entirety]. However, many-particle aggregates or colloid-based nanostructures are reported to provide isotropic and inhomogeneous SPRs mediated EM field localization [M. K. Hossain, G. G. Huang, T. Kaneko and Y. Ozaki, *Chem. Phys. Lett.,* 2009, 477, 130-134.; and T. Itoh, V. Biju, M. Ishikawa, Y. Kikkawa, K. Hashimoto, A. Ikehata and Y. Ozaki, *J. Chem. Phys.,* 2006, 124, 134708-1-134708-6.—each incorporated herein by reference in its entirety]. Furthermore, a broad SPR excitation peak, which is much different from the individual narrow excitations of isolated hotsites [L. Novotny and B. Hecht, *Principles of Nano-Optics*, Cambridge University Press, Cambridge, 2006.—incorporated herein by reference in its entirety]. Hence, limited-particle aggregates or nanostructures with a unique assembly are essential and indispensable to understand SERS enhancement as well as polarization dependent and polarization selective SERS characteristics. However, most of the SERS studies have considered a single dimer where the polarization effect was explained, but not the ensemble enhancement [Z. Li and H. Xu, *J. Quant. Spectros. & Radia. Trans.,* 2007, 103, 394-401; and K. D. Alexander, M. J. Hampton, S. Zhang, A. Dhawan, H. Xu and R. A. Lopeza, *J. Raman Spectrosc.,* 2009, 40, 2171-2175; and D. F. Zhang, Q. Zhang, L. Y. Niu, L. Jiang, P. G. Yin and L. Guo, *J. Nanopar. Res.,* 2011, 13, 3923-3928—each incorporated herein by reference in its entirety]. Further, fixed polarization has been adopted for macroscopic samples, and hence, variations in the interstitials and SPRs have hardly been explored.

In view of the forgoing, one object of the present disclosure is to provide anisotropic gold nanoassemblies comprising nanoparticles neither in physical contact nor agglomerated but rather separated by small interparticle gaps that provide high SERS activity. Using such anisotropic gold nanoassemblies allows fine tuning of polarization dependent and polarization selective SERS measurements and background fluorescence signals with emphasis on spectroscopic measurements with reference to available active sites (i.e. localized EM fields) rather than diffraction limited imaging. A further aim of the present disclosure is a method and apparatus comprising the SERS active gold nanoassembly for measuring the surface enhanced Raman scattering (SERS) signal of an analyte and/or detecting an analyte. A further aim of the present disclosure is to provide a simple one step evaporation assisted nanoparticle assembly process to fabricate the anisotropic gold nanoassemblies.

BRIEF SUMMARY OF THE INVENTION

According to a first aspect, the present disclosure relates to a surface enhanced Raman scattering (SERS) active nanoassembly comprising i) a glass layer and ii) gold nanoparticles immobilized on the glass layer wherein the gold nanoparticles are anisotropically assembled as a monolayer double row having a long axis.

In one embodiment, the gold nanoparticles have a spherical morphology and an average diameter of 25-75 nm.

In one embodiment, the gold nanoparticles are anisotropically assembled as a monolayer double row having a long axis of 1-200 µm in length.

In one embodiment, the gold nanoparticles are discrete and separated by interparticle gaps of 0.5-10 nm.

In one embodiment, the surface enhanced Raman scattering (SERS) active nanoassembly has a SERS enhancement factor of at least $10^4$.

In one embodiment, the surface enhanced Raman scattering (SERS) active nanoassembly is substantially free of surfactants, capping reagents and/or linkers.

In one embodiment, the surface enhanced Raman scattering (SERS) active nanoassembly further comprises at least one additional SERS active metal selected from the group consisting of silver, copper, platinum, palladium and alloys thereof.

According to a second aspect, the present disclosure relates to an apparatus for detecting an analyte comprising i) the surface enhanced Raman scattering nanoassembly wherein an analyte is adsorbed onto the surface enhanced Raman scattering nanoassembly ii) a radiation source and iii) a detector wherein the radiation source provides incident radiation on the analyte and the detector is positioned to receive scattered radiation from the analyte and wherein the scattered radiation is used to detect the analyte.

In one embodiment, the apparatus further comprises additional optical elements to process, focus and/or deflect either the incident radiation from the radiation source or the scattered radiation from the analyte.

In one embodiment, the analyte comprises at least one biological molecule selected from the group consisting of a protein, a deoxyribonucleic acid sequence, a ribonucleic acid sequence, an amino acid, a peptide, a nucleotide, a nucleoside, and a neurotransmitter.

In one embodiment, the analyte comprises at least one dye.

In one embodiment the radiation source is a krypton ion laser providing incident radiation having a wavelength of 400-800 nm or a helium-neon gas laser providing incident radiation having a wavelength of 500-650 nm.

In one embodiment, the detector is a multichannel charge couple device (CCD).

According to a third aspect, the present disclosure relates to a method for measuring the surface enhanced Raman scattering (SERS) signal of an analyte comprising i) adsorbing an analyte onto the gold nanoparticles of the the surface enhanced Raman scattering (SERS) active nanoassembly to form a substrate ii) exciting the substrate with a light source to produce a Raman signal and iii) detecting and measuring the Raman signal of the substrate wherein the analyte has a Raman signal that is enhanced relative to the Raman signal of the analyte without the surface enhanced Raman scattering (SERS) active nanoasssembly.

In one embodiment, the analyte has a Raman signal that is enahanced $10^4$-$10^{15}$ fold relative to the Raman signal of a substantially similar analyte measured by substantially similar methods without the surface enhanced Raman scattering (SERS) active nanoassembly in terms of the Raman signal intensity.

In one embodiment, the light source is polarizable and the Raman signal of the analyte is maximally enhanced when the light source is polarized along the plane of the long axis of the gold nanoparticles of the surface enhanced Raman scattering nanoassembly and wherein the Raman signal of the analyte is minimally enhanced when the light source is polarized perpendicular to the plane of the long axis of the gold nanoparticles of the surface enhanced Raman scattering nanoassembly.

In one embodiment, the gold nanoparticles are discrete and separated by interparticle gaps and the surface enhanced Raman scattering nanoassembly has maximum electromagnetic near field distributions in the inerparticle gaps in the range of 10-50 dBV/m.

In one embodiment, the light source has a wavelength of 200-1100 nm that excites surface plasmons of the surface enhanced Raman scattering (SERS) active nanoassembly.

According to a fourth aspect, the present disclosure relates to a method for producing the surface enhanced Raman scattering nanoassembly comprising i) washing glass slides with an alcohol ii) immersing the washed glass slides in a suspension comprising gold nanoparticles 25-75 nm in diameter and the alcohol, evaporating the excess alcohol to form the surface enhanced Raman scattering nanoassembly.

In one embodiment, the washed glass slides are immersed at a 15-45° angle releative to the surface of the solution.

The foregoing paragraphs have been provided by way of general introduction, and are not intended to limit the scope of the following claims. The described embodiments, together with further advantages, will be best understood by reference to the following detailed description taken in conjunction with the accompanying drawings.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein.

DETAILED DESCRIPTION OF THE EMBODIMENTS

Figure 1:
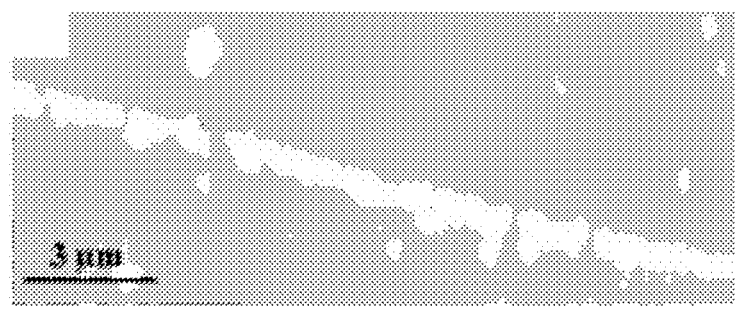
FIG. 1 is an atomic force microscopy (AFM) image of the prepared surface enhanced Raman scattering (SERS) active nanoassembly of 50 nm gold nanoparticles.

Referring now to the drawings, wherein, like reference numerals designate identical or corresponding parts throughout the several views.

According to a first aspect, the present disclosure relates to a surface enhance Raman scattering (SERS) active nanoassembly. Surface enhanced Raman spectroscopy or surface enhanced Raman scattering (SERS) refers to a surface sensitive technique that enhances Raman scattering by molecules adsorbed on rough metal surfaces or by nanostructures. Therefore, one object of the present disclosure is to provide a nanoassembly that increases the Raman scattering and signal of adsorbed molecules before, during, and/or after excitation.

Raman spectroscopy is a spectroscopic technique used to observe vibrational, rotational and other low frequency modes in a system. Raman spectroscopy is commonly used in chemistry to provide a fingerprint by which molecules can be identified. It relies on inelastic scattering, or Raman scattering, of monochromatic light, usually from a laser in the visible, near infrared, or near ultraviolet range. The laser light interacts with molecular vibrations, phonons or other excitations in the system, resulting in the energy of the laser photons being shifted up or being shifted down. The Raman interaction leads to two possible outcomes: i) the material absorbs energy and the emitted photon has a lower energy than the absorbed photon, known as Stokes Raman scattering or ii) the material loses energy and the emitted photon has a higher energy than the absorbed photon, known as anti-Stokes Raman scattering. The energy difference between the absorbed and emitted photon corresponds to the energy difference between two resonant states of the material and is independent of the absolute energy of the photon. The shift in energy gives information about the vibrational modes in the system.

A particular subset of spectroscopy within the realm of Raman spectroscopy is surface enhanced Raman spectroscopy (SERS). SERS refers to the observation that certain molecules adsorbed on specially prepared metallic surfaces possess Raman spectrum of greatly increased intensity. Under external radiation an "active site", "magic site" or "hot site" appears at junctions of or in the vicinity of nanoparticles corresponding to the phenomenon of localized surface plasmon resonances (LSPRs) mediating intense electromagnetic (EM) field distribution. There are two primary theories to the mechanism of the enhancement effect of SERS. The electromagnetic theory proposes the excitation of localized surface plasmons, while the chemical theory proposes the formation of charge-transfer complexes. In the electromagnetic theory, the increase in intensity of the Raman signal for adsorbates on particular surfaces occurs because of an enhancement in the electric field provided by the surface.

The surface enhanced Raman scattering (SERS) active nanoassembly of the present disclosure comprises a glass layer. The nature of this layer is not viewed as particularly limiting and any suitable material of varying size, shape and texture (i.e. smooth, porous, roughened, corrugative and/or etched) may be envisioned that is non-conductive and provides suitable SERS activity. In a preferred embodiment, the layer is inert, preferably inert such as glass or silicon, preferably glass. The surface enhanced Raman scattering (SERS) active nanoassembly further comprises gold nanoparticles immobilized on the glass layer, wherein the gold nanoparticles are anisotropically assembled as a monolayer double row having a long axis. The glass layer having gold nanoparticles immobilized on it in a monolayer double row is referred to herein as the "SERS active nanoassembly", "active nanoassembly" or "nanoassembly".

Gold (Au) is a chemical element exhibiting a face centered cubic crystal structure. In its purest form, it is a bright, slightly reddish yellow, dense, soft, malleable and ductile metal. Chemically, gold is a transition metal and a group 11 element. It is one of the least reactive chemical elements and is solid under standard conditions. The metal occurs frequently in elemental (native) form, in solid solution series with the native element silver and also naturally alloyed with copper, platinum and/or palladium. Less commonly, it occurs in minerals as gold compounds, often with tellurium. The most common oxidation states of gold include $^{+}1$ known as gold (I), Au(I) or aurous compounds and $^{+}3$ known as gold (III), Au(III) or auric compounds. Gold ions are readily reduced and precipitated as metal.

In a preferred embodiment, the gold nanoparticles of the present disclosure substantially comprise elemental gold. The term "gold nanoparticle" as used herein refers to an elemental gold rich material (i.e. greater than 50%, more preferably greater than 60%, more preferably greater than 70%, more preferably greater than 75%, more preferably greater than 80%, more preferably greater than 85%, more preferably greater than 90%, more preferably greater than 95%, most preferably greater than 99% elemental gold by weight), which is immobilized in a monolayer double row assembly onto a glass layer In addition to elemental gold, various non-elemental gold materials including, but not limited to, gold alloys, metals and non-metals may be present in the gold nanoparticle. The total weight of these non-elemental gold materials relative to the total weight percentage of the gold nanoparticles is typically less than 30%, preferably less than 20%, preferably less than 15%, preferably less than 10%, more preferably less than 5%, more preferably less than 4%, more preferably less than 3%, more preferably less than 2%, more preferably less than 1%.

In addition to elemental gold, it is envisaged that the present disclosure may be adapted to incorporate gold alloys as the gold nanoparticles. Exemplary gold alloys include, but are not limited to, alloys with copper and silver (colored gold, crown gold, electrum), alloys with rhodium (rhodite), alloys with copper (rose gold, tumbaga), alloys with nickel and palladium (white gold) as well as alloys including the addition of platinum, manganese, aluminum, iron, indium and other appropriate elements or mixtures thereof. In one embodiment, it is envisaged that the present disclosure may be adapted in such a manner that the gold nanoparticles substantially comprise a gold alloy.

In addition to gold, it is envisaged that the present disclosure may be adapted to incorporate at least on additional SERS active metal (capable of surface plasmon resonance under light from 200-1100 nm) selected from the group consisting of silver, copper, platinum, palladium and alloys thereof. These metals may be in the form of nanoparticles and may be randomly or non-randomly arranged amongst the gold nanoparticles of the present disclosure or in some embodiments fully substituted for the gold nanoparticles of the present disclosure. In a preferred embodiment less than 60% of the nanoparticles are an additional SERS active metal, preferably less than 50%, preferably less than 40%, preferably less than 30%, preferably less than 25%, preferably less than 20%, preferably less than 15%, preferably less than 10%, preferably less than 5% of the nanoparticles are an additional SERS active metal.

Nanoparticles are particles between 1 and 100 nm ($10^2$ and $10^7$ atoms) in size. A particle is defined as a small object that behaves as a whole unit with respect to its transport and properties. The exceptionally high surface area to volume ratio of nanoparticles may cause the nanoparticles to exhibit significantly different or even novel properties from those observed in individual atoms/molecules, fine particles and/or bulk materials. Nanoparticles may be classified according to their dimensions. Three-dimensional nanoparticles have all dimensions of less than 100 nm, and generally encompass isodimensional nanoparticles. Examples of three-dimensional nanoparticles include, but are not limited to, nanoparticles, nanospheres, nanogranules and nanobeads. Two-dimensional nanoparticles have two dimensions of less than 100 nm, generally including diameter. Examples of two-dimensional nanoparticles include, but are not limited to, nanotubes, nanofibers and nanowhiskers. One-dimensional nanoparticles have one dimension of less than 100 nm, generally thickness. Examples of one-dimensional nanoparticles include, but are not limited to, nanosheets, nanoplatelets, nanolaminas and nanoshells. The gold nanoparticles of the present disclosure are preferably three-dimensional nanoparticles, but may also be one-dimensional, two-dimensional, three-dimensional or mixtures thereof.

Nanoparticles are named for the real-world shapes that they appear to represent. These morphologies sometimes arise spontaneously as an effect of the synthesis or from the innate crystallographic growth patterns of the materials themselves. Some of these morphologies may serve a purpose, such as bridging an electrical junction. In a preferred embodiment, the gold nanoparticles of the present disclosure are in the form of a nanoparticle, which is spherical or substantially spherical (e.g. oval, oblong, etc.) in shape. Alternatively, it is envisaged that the gold nanoparticles may have a more polygonal shape and may be generally cubic or rectangular. However, the gold nanoparticles disclosed herein may have various shapes other than spheres and may be of any shape that provides desired SERS activity and/or desired properties in the resulting nanoassembly. In a preferred embodiment, the gold nanoparticles have a spherical morphology.

In one embodiment, the gold nanoparticles of the present disclosure are envisaged to be synthesized and formed into a variety of morphologies including, but not limited to, nanoparticles, nanosheets, nanoplatelets, nanocrystals, nanospheres, nanorectangles, nanotriangles, nanopentagons, nanohexagons, nanoprisms, nanodisks, nanocubes, nanowires, nanofibers, nanoribbons, nanorods, nanotubes, nanocylinders, nanogranules, nanowhiskers, nanoflakes, nanofoils, nanopowders, nanoboxes, nanostars, tetrapods, nanobelts, nanaourchins, nanofloweres, etc. and mixtures thereof.

In one embodiment, the gold nanoparticles have uniform shape. Alternatively, the shape may be non-uniform. As used herein, the term "uniform" refers to an average consistent shape that differs by no more than 10%, by no more than 5%, by no more than 4%, by no more than 3%, by no more than 2%, by no more than 1% of the distribution of gold nanoparticles having a different shape. As used herein, the term "non-uniform" refers to an average consistent shape that differs by more than 10% of the distribution of gold nanoparticles having a different shape. In one embodiment, the shape is uniform and at least 90% of the gold nanoparticles are spherical or substantially circular, and less than 10% are polygonal or substantially square. In another embodiment, the shape is non-uniform and less than 90% of the gold nanoparticles are spherical or substantially circular, and greater than 10% are polygonal or substantially square.

Nanoparticle characterization may be used to establish understanding and control of nanoparticle and nanoassembly synthesis, assembly and application. In one embodiment, it is envisioned that characterization is done using a variety of techniques. Exemplary techniques include, but are not limited to, electron microscopy (TEM, SEM), atomic force microscopy (AFM), ultraviolet-visible spectroscopy (UV-Vis), dynamic light scattering (DLS), X-ray photoelectron spectroscopy (XPS), X-ray fluorescence (XRF), powder X-ray diffraction (XRD), energy dispersive X-ray spectroscopy (EDX), thermogravimetric analysis (TGA), Fourier transform infrared spectroscopy (FTIR), matrix-assisted laser desorption/ionization time-of-flight mass spectrometry (MALDI-TOF), Rutherford backscattering spectrometry (RBS), dual polarization interferometry and nuclear magnetic resonance or mixtures thereof.

The size of gold nanoparticles may also dictate the level of SERS activity and enhancement for the nanoassembly described herein. For spherical or substantially spherical gold nanoparticles, average particle size refers to the average longest linear diameter of the gold nanoparticles. For non-spherical gold nanoparticles, such as cubes, squares and/or rectangles the average particle size may refer to the longest linear dimension and any of the length, width or height. In a preferred embodiment, the gold nanoparticles of the present disclosure are mondispersed with an average particle size of 25-75 nm, preferably 30-70 nm, preferably 35-65 nm, preferably 40-60 nm, preferably 45-55 nm, or 50 nm. In another embodiment, the gold nanoparticles of the present disclosure are monodispersed with an average particle size of 1-250 nm, preferably 1-200 nm, preferably 1-150 nm, preferably 5-100 nm, preferably 5-75 nm, preferably 10-50 nm. The size may vary from these ranges and still provide an acceptable SERS active nanoassembly.

In a preferred embodiment, the gold nanoparticles of the present disclosure are monodisperse, having a coefficient of variation or relative standard deviation, expressed as a percentage and defined as the ratio of the particle size standard deviation ($\sigma$) to the particle size mean ($\mu$) multiplied by 100 of less than 25%, preferably less than 10%, preferably less than 8%, preferably less than 6%, preferably less than 5%, preferably less than 4%, preferably less than 3%, preferably less than 2%. In a preferred embodiment, the gold nanoparticles of the present disclosure are monodisperse having a particle size distribution ranging from 80% of the average particle size to 120% of the average particle size, preferably 90-110%, preferably 95-105% of the average particle size.

In a preferred embodiment, the gold nanoparticles are entirely discrete taken to include monolayer and non-agglomerated. The gold nanoparticles are discrete and separated by interparticle gaps or an interparticle distance of 0.5-10 nm, preferably 0.75-9 nm, preferably 1.0-8 nm, preferably 1.25-7 nm, preferably 1.5-6 nm, preferably 1.75-5.5 nm, most preferably 2.0-5.0 nm. The interparticle distance refers to the shortest distance between the outer edges of two neighboring gold nanoparticles. The properties of gold nanoparticles may change when particles aggregate and these interparticle gaps provide the hotsites or active sites for SERS enhancement. In a preferred embodiment, the gold nanoparticles of the present disclosure have an average surface to surface interparticle distance of less than 200% of their average particle size, preferably less than 150% of their average particle size, preferably less than 100% of their average particle size, preferably less than 50% of their average particle size, preferably less than 25% of their average particle size, preferably less than 10% of their average particle size, preferably less than 5% of their average particle size. For example, spherical gold nanoparticles having a 50 nm diameter may be separated by an average interparticle distance of 2.5-100 nm, preferably 2.5-50 nm, preferably 2.5-25 nm, preferably 2.5-5 nm.

In a preferred embodiment the gold nanoparticles are immobilized on the glass substrate by adsorption defined as the adhesion of atoms, ions or molecules to a surface creating a film of gold nanoparticles immobilized on the glass layer. All bonding requirements (be they ionic, covalent, or metallic) of the constituent atoms of the material are filled by other atoms in the material. The exact nature of the bonding depends on the details of the species involved but the process can generally be classified physisorption (characteristic of weak van der Waals forces) or chemisorption (characteristic of covalent bonding) or due to electrostatic attraction. As used herein "immobilized", "immobilizing", "adsorbed", "adsorbing", "bound" or "binding" refers to the adsorption and/or chemical binding via strong atomic bonds (e.g. ionic, metallic and covalent bonds) and/or weak bonds such as van der Waals, hydrogen. In a preferred embodiment, the gold nanoparticles are physisorbed onto the glass layer, leaving the chemical species of both materials intact. In a preferred embodiment, the SERS active nanoassembly is substantially free of surfactants, capping reagents and/or linkers that are often used to aid the immobilization of SERS active substrates. For SERS applications, residual surfactants, capping reagents and/or linkers may prevent Raman analytes from coming close to the center of the interparticle gaps or hotsites. In addition, surfactants, capping reagents and/or linkers induce a huge background emission, which is unfavorable for the specific detection of analytes.

Anisotropy is the property of being directionally dependent, as opposed to isotropy, which implies identical properties in all directions. It can be defined as a difference, when measured along different axes, in a material's physical or mechanical properties, in terms of the present invention it refers to the surface enhanced Raman scattering (SERS) activity of the nanoassembly described herein. In a preferred embodiment, the gold nanoparticles of the present disclosure are anisotropically assembled as a monolayer double row having a long axis. In a preferred embodiment the monolayer double row is linear, it is equally envisioned that the monolayer double layer may have curvature. The glass layer of the present disclosure may have a single or a plurality of monolayer double row assemblies of gold nanoparticles and they may be spaced 100-1000 μm from each other, preferably 250-750 μm from each other or 500 μm from each other.

Figure 2A:
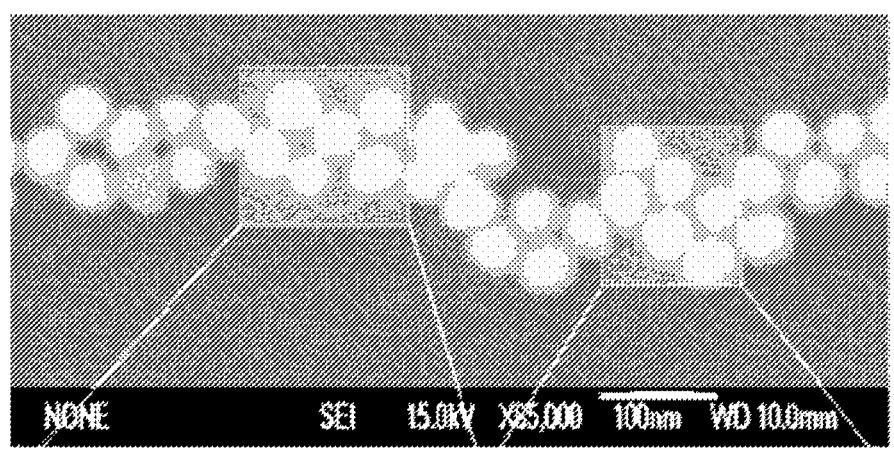
FIG. 2A is a scanning electron microscopy (SEM) image of the prepared SERS active nanoassembly.
Figure 2B:
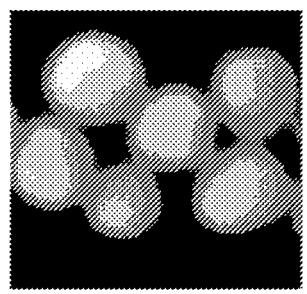
FIG. 2B is a SEM image of the magnified view of a segment of the prepared SERS active nanoassembly filtered by 100% contrast and 50% low brightness to indicate the interparticle gaps between two adjacent nanoparticles.
Figure 2C:
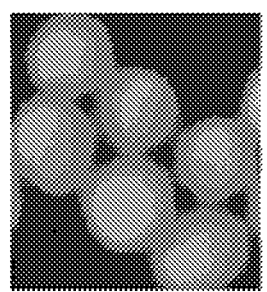
FIG. 2C is a SEM image of the magnified view of a segment of the prepared SERS active nanoassembly filtered by 100% contrast and 50% low brightness to indicate the interparticle gaps between two adjacent nanoparticles.

The monolayer double row of the present disclosure comprises a repeating "doublet" of two gold nanoparticles (see FIG. 2A, FIG. 2B and FIG. 2C). In one embodiment, the monolayer double row is substantially free from anomalies and comprises a uniform monolayer double row of two gold nanoparticles over the entire length of the long axis. As used herein, an "anomaly" is defined as any section of the monolayer double row that is not a monolayer double row (i.e. a single row, triple row, bilayer, etc. section). In a preferred embodiment, the monolayer double row is greater than 70% free of anomalies, preferably greater than 75%, preferably greater than 80%, preferably greater than 85%, preferably greater than 90%, preferably greater than 95% free of anomalies. In another embodiment these anomalies occur with low frequency and the monolayer comprises 3-100 doublets without an anomaly, preferably 5-50 doublets, preferably 5-25 doublets, preferably 5-10 doublets without an anomaly.

In a preferred embodiment, the long axis of the monolayer double row has a length of 1-200 μm, preferably 1-150 μm, preferably 1-100 μm, preferably 5-90 μm, preferably 10-80 μm, preferably 15-75 μm, preferably 20-70 μm, preferably 30-60 μm, preferably 40-50 μm. In a preferred embodiment, the monolayer double row has a width measured perpendicular to the long axis of 50-200 nm, preferably 60-150 nm, preferably 75-150 nm, preferably 85-125 nm, preferably 100-125 nm. In a preferred embodiment, the SERS active nanoassembly of the present disclosure and the monolayer double row of gold nanoparticles comprise 50-10,000 discrete gold nanoparticles, preferably 100-8000, preferably 200-6000, preferably 300-5000, preferably 400-4000, preferably 500-3000 discrete gold nanoparticles.

As used herein, the SERS "enhancement factor" refers to the extent that surface enhancement increases the intensity of Raman scattering. In a preferred embodiment, the SERS enhancement factor refers to the analytical enhancement factor (AEF). The AEF can be calculated given that $C_{RS}$ and $C_{SERS}$ are the concentrations detected for non-SERS and SERS activity, respectively, $I_{RS}$ is the Raman intensity produced for a concentration under non-SERS conditions and $I_{SERS}$ is the Raman intensity for a concentration under SERS substrate activity using formula (I):

$$AEF = \frac{C_{RS} I_{SERS}}{C_{SERS} I_{RS}} \qquad (I)$$

In one embodiment, the surface enhanced Raman scattering (SERS) active nanoassembly of the present disclosure has a SERS enhancement factor of at least $10^4$, more preferably $10^4$-$10^{14}$, more preferably $10^5$-$10^{12}$, more preferably $10^6$-$10^{11}$, more preferably $10^7$-$10^{10}$. In another embodiment, the SERS enhancement factor may refer to the average SERS enhancement factor or SERS substrate enhancement factor (SSEF) where the SERS intensity is normalized by the number of adsorbed molecules rather than by the volume concentration in the starting solution. In another embodiment, the SERS enhancement factor may refer to the single-molecule enhancement factor (SMEF).

According to a second aspect, the present disclosure relates to an apparatus for detecting an analyte including the surface enhanced Raman scattering (SERS) active nanoassembly in any of its embodiments wherein an analyte is adsorbed onto the surface of the SERS active nanoassembly, a radiation source and a detector wherein the radiation source provides incident radiation on the analyte and the detector is position to receive scattered radiation from the analyte and wherein the scattered radiation is used to detect the analyte. Any suitable surface enhanced Raman scattering (SERS) apparatus may be used in combination with the SERS active nanoassembly in any of its embodiments of the present disclosure. Two exemplary apparatus set ups are shown in FIG. 6B and FIG. 7B.

As used herein, the term "analyte" refers to a chemical or biological entity that can be identified, detected and/or quantified by an analytic process such as the method of measuring the surface enhanced Raman scattering (SERS) signal of the analyte described herein. In a preferred embodiment the analyte is a chemical or biological entity that can be detected or quantified by SERS. A "biological analyte" includes, but is not limited to, microorganisms, cells, cell products, and/or biological molecules. A microorganism refers to a microscopic living system including, but not limited to, viral particles such as virions, prions, or viriods, bacteria, fungi, archae, protists, microscopic algae, plankton, planarian and mixtures thereof. A cell includes both prokaryotic and eukaryotic cells, including both natural and recombinant cells and cell products include constituents of cells such as cell membranes and organelles.

As used herein, "biological molecule" refers to a molecule that is produced by a living organism and also refers to synthetic analogs of such molecules. Examples of such biological molecules include, but are not limited to, carbohydrates such as glucose, disaccharides and polysaccharides, proteins, lipids, lipid bilayers, nucleic acids such as DNA and RNA. Biological molecules may also refer to small molecules, including monomers and oligomers of other biological molecules, i.e. nucleic acids, nucleotides, fatty acids and the like. The biological molecules may be naturally occurring or synthetic and may include both naturally occurring and synthetic portions. The term biological molecule also refers to derivative of biological molecules, such as conjugated nanoparticles. In a preferred embodiment, the analyte comprises at least one biological molecule selected from the group consisting of a protein, a deoxyribonucleic acid sequence, a ribonucleic acid sequence, an amino acid, a peptide, a nucleotide, a nucleoside and a neurotransmitter.

A "chemical analyte" refers to an analyte that is not a biological analyte as defined above. In one embodiment, chemical analytes are non-biological molecules and may be organic, inorganic or a combination of organic or inorganic moieties. The chemical analyte may be synthetic or naturally occurring, such as a synthetic polymer or synthetic polymer nanoparticles. In another embodiment the analyte may comprise a probe molecule referring to biological or chemical analytes that are immobilized on the nanoassembly and bind or interface with another component of the analyte. Not limiting examples include, but are not limited to, antibody-antigen, protein-ligand, protein-aptamer, paired nucleotides and the like.

Dyes which strongly adsorb in the visible light range and are therefore in resonant conditions and are an important family of SERS probes. Acidic dyes are dyes that have a negative charge causing them to bind or associate with positively charged structures; representative examples include nigrosine, picric acid, eosin, acid fuschin and the like. Basic dyes are dyes that have a positive charge causing them to bind or associate with negatively charged structures; representative examples include crystal violet, methylene blue, safranin, basic fuschin and the like. Neutral dyes are generally formed from precipitation in which aqueous acidic and basic dyes are combined; representative examples include eosinate of methylene blue, giesma and the like. In terms of the present disclosure, the analyte may comprise a dye and the dye may be acidic, basic or neutral, preferably basic, preferably crystal violet (CV, $C_{25}H_{30}ClN_3$).

Crystal violet (also known as gentian violet, methyl violet 10B or hexamethyl paraosaniline chloride) is a triarylmethane dye. When dissolved in water the dye has a blue-violet color with an absorbance maximum at 590 nm and an extinction coefficient of 87,000 M-1 cm-1. The color of the dye depends on the acidity of the solution. At a pH of 1.0 the dye is green with absorption maxima at 420 nm and 620 nm, while in a strongly acidic solution the dye is yellow with an absorption maximum at 420 nm. It is envisioned that other dyes may be used in lieu of crystal violet. Suitable dyes may be selected from the group including, but not limited to, methyl violet, fluorescein, prussian blue, egyptian blue, methyl blue, methylene blue, new methylene blue, han purple, potassium ferrocyanide, potassium ferricyanide, methyl violet 6B, methyl violet 2B, fuchsine, ararosaniline, ranailine, new fuchsine, magenta II, bromocresol green, malachite green, xanthene dyes (fluorescein, eosine, phloxine, eythrosine, rose bengal), rhodamine dyes (rhodamine 6G), benzotriazole dyes (benzotriazole BTA, benzotriazole dye 2 BTZ), anthraquinone dyes, flavone dyes, arylmethane dyes, protoberberine dyes and mixtures thereof.

In a preferred embodiment, the radiation source is a laser source. Any suitable radiation source may be used and is envisioned. Exemplary laser sources include, but are not limited to, gas lasers, chemical lasers, excimer lasers, metal vapor lasers, solid state lasers, titanium sapphire lasers, fiber lasers, photonic crystal lasers, semiconductor lasers, dye lasers, and free electron lasers.

In a preferred embodiment, the radiation source is an ion laser, preferably a krypton or argon laser, more preferably a krypton laser. An ion laser is a gas laser which uses an ionized gas as its lasing medium. An argon laser is one of the families of ion lasers that use a noble gas as the active medium. Argon lasers emit at 13 wavelengths through the visible, ultraviolet, and near-visible spectrum at 351.1 nm, 363.8 nm, 454.6 nm, 457.9 nm, 465.8 nm, 472.7 nm, 476.5 nm, 488.0 nm, 496.5 nm, 501.7 nm, 514.5 nm, 528.7 nm and 1092.3 nm, also frequency doubled to provide 244 nm and 257 nm. If an argon laser is used it is preferably operated at 488.0 or 514.5 nm. A krypton laser is an ion laser using krypton ions as a gain medium, pumped by electric discharge. Krypton lasers emit at several wavelengths through the visible spectrum at 406.7 nm, 413.1 nm, 415.4 nm, 468.0 nm, 476.2 nm, 482.5 nm, 520.8 nm, 530.9 nm, 568.2 nm, 647.1 nm, 676.4 nm, 752.5 nm, 799.3 nm. If a krypton laser is used it is preferably operated at 530.9 or 647.1 nm. Other exemplary ion lasers include, but are not limited to Argon/Krypton lasers, Helium/Cadmium lasers (442 nm and 325 nm), Copper Vapor lasers (578 nm and 510 nm), Xenon lasers, Iodine lasers and Oxygen lasers. In a most preferred embodiment, the radiation source is a $Kr^+$ laser operating at 647.1 nm.

In another embodiment, the radiation source may be a gas laser, preferably a helium-neon laser. A helium-neon laser or HeNe laser is a type of gas laser whose gain medium consists of a mixture of helium and neon (10:1) inside of small bore capillary tube, usually excited by a DC electrical discharge. The pressure inside the tube is 1 mm of Hg. The most widely used HeNe laser operates at a wavelength of 632.8 nm in the red part of the visible spectrum. HeNe lasers emit at several wavelengths at 543.5 nm, 593.9 nm, 611.8 nm, 632.8 nm, 1.1523 μm, 1.52 μm, 3.3913 μm. If a HeNe laser is used it is preferably operated at 632.8 nm.

In another embodiment, the radiation source may be a laser diode, an electrically pumped semiconductor laser in which the active laser medium is formed by a p-n junction of a semiconductor diode. Exemplary appropriate types of laser diodes include, but are not limited to, double heterostructure lasers, quantum well lasers, quantum cascade lasers, separate confinement heterostructure lasers, distributed Bragg reflector lasers, distributed feedback lasers, vertical cavity surface emitting lasers (VCSELs), vertical external cavity surface emitting lasers (VECSELs) and external cavity diode lasers. If a laser diode laser is used it is preferably operated at 785 nm or 830 nm.

In a preferred embodiment, any suitable detector may be used and is envisioned. Two main categories of optical detectors are used in typical SERS apparatuses: single channel and multichannel. Single channel detectors have just one element that accepts light through the exit slit of a monochromator or polychromator. An apparatus containing a single channel detector produces a spectrum by rotating the monochromator or polychromator grating and recording one data point for each grating position. In contrast, multichannel detectors collect many data points simultaneously without moving a grating or any other part of the spectrograph. This allows much more efficient data collection than for single channel detectors, as large amounts of spectral data can be collected in a single exposure. In terms of the present disclosure, the detector may be single channel or multichannel.

Exemplary single channel detectors include, but are not limited to, a single photodiode, a photomultiplier (PMT), and an avalanche photodiode (APD). A photodiode is a semiconductor device that converts light into current; the current is generated when photons are adsorbed in the photodiode. Photodiodes may contain optical filters, built-in lenses and may have large or small surface areas. A photomultiplier or photomultiplier tube (PMT) is a photoemissive device in which the absorption of a photon results in the emission of an electron. These detectors work by amplifying the electrons generated by a photocathode exposed to a photon flux. PMTs are extremely sensitive detectors of light in the ultraviolet, visible and near infrared ranges and multiply current in multiple dynode stages. An avalanche photodiode is a highly sensitive semiconductor electronic device that exploits the photoelectric effect to convert light to electricity that operates at high speeds and high gain by applying a reverse bias. APDs can be thought of as photo-detectors that provide built in first stage of gain through avalanche multiplication and are regarded as the semiconductor analog to photomultipliers. By applying a high reverse bias voltage, APDs show an internal current gain effect due to impact ionization (avalanche effect). In terms of the present disclosure, the detector of the apparatus may be single channel and may be single photodiode, a photomultiplier and/or an avalanche photodiode.

Exemplary multichannel detectors include, but are not limited to, a diode array and a charge coupled device (CCD). A diode array detector of photodiode array detector (DAD or PAD) refers to a one-dimensional array of hundreds or thousands of photodiodes that can be used as a position sensor allowing for high speed parallel read out. The DAD has multiple sample side light receiving sections allowing them to obtain information over a wide range of wavelengths at one time. A charge coupled device (CCD) is a silicon based multichannel array detector of light and broadly a device for the movement of electrical charge, usually from within the device to an area where charge can be manipulated, for example conversion into a digital value. This is achieved by shifting the signals between stages within the device one at a time. CCDs move charge between capacitive bins in the device, with the shift allowing for the transfer of charge between bins. The CCD is a major piece of technology in digital imaging. In a CCD image sensor, pixels are represented by p-doped MOS capacitors. The capacitors are biased above the threshold for inversion when image acquisition begins, allowing the conversion of incoming photons into electron charges at the semiconductor oxide interface; the CCD is then used to read out these charges. The term CCD may also refer to electron multiplying CCDs, CCD cameras, frame transfer CCDs and intensified CCDs. In terms of the present disclosure, the detector of the apparatus may be multichannel and may be a diode array and/or a charge coupled device (CCD), preferably a charge coupled device (CCD).

In one embodiment, the apparatus may further comprise additional optical elements to process the radiation such as optical elements that focus and/or deflect (e.g. lens and/or mirrors) the radiation from the radiation source to provide incident radiation and/or optical elements that focus and/or deflect the scattered radiation to provide the scattered radiation to the detector. Exemplary additional optical elements include, but are not limited to a filter, a reflector, an attenuator, a lens, an optical filter, a notch filter, a holographic notch filter, an edge filter, a laser rejection filter, imaging optics, focusing optics, collection optics, an objective lens, a mirror, a beam splitter, a window, a grating, a prism, a laser line rejection device, a wavelength selection device, a polychromator, a spectrometer, a monochromator, a half wave plate, a rotary polarizer and mixtures thereof. In another embodiment, the SERS active nanoassembly of the apparatus may be on a stage. The stage may be connected to a controller which may move the stage in linear and/or rotational translations vertically and/or horizontally as desired, such that different portions of the nanoassembly may be irradiated by incident radiation and analyzed as desired.

In another embodiment, the apparatus may further comprise additional imaging elements. Exemplary additional imaging elements may include, but are not limited to a white light (i.e. Xe lamp) dark field condenser combination for observing LSPR images, a CCD camera or a high resolution CCD camera for observing SPR and SERS imaging as opposed to spectral measurements, a variety of monitors and readouts for the images and mixtures thereof. In another embodiment, the apparatus may further comprise analytical equipment that may be programmed to process the information from the detector and generate a Raman spectrum, this may be controlled by a computer. In another embodiment, the same or different analytical equipment may process the Raman spectrum to identify at least one analyte, this may be controlled by a computer. The components of the apparatus described herein may all or partially be automated and/or synchronized with other components of the apparatus.

According to a third aspect, the present disclosure relates to a method for measuring the surface enhanced Raman scattering (SERS) signal of an analyte including adsorbing at least one analyte onto the gold nanoparticles of the SERS active nanoassembly in any of its embodiments to form a substrate, exciting the substrate with an incident light source, to produce a Raman signal, preferably a SERS signal and detecting and measuring the scattered radiation of the Raman signal of the substrate, wherein the analyte has a Raman signal that is enhanced relative to the Raman signal of the analyte without the SERS active nanoassembly. This method is envisaged to be adapted to be performed using any suitable SERS apparatus in combination with the SERS active nanoassembly, including the apparatus in any of its embodiments described herein as an aspect of the present disclosure.

One or more analytes, as previously described, are adsorbed, as previously described onto the gold particles of the SERS active nanoassembly. As used herein, a "substrate" refers to the SERS active gold nanoassembly with at least one analyte completely or partially adsorbed onto the nanoassembly. In one embodiment, at least one analyte is adsorbed onto at least one gold nanoparticle; the analyte may be adsorbed onto two or more gold nanoparticles. In another embodiment, the analyte is adsorbed such that at least a portion is within or exposed to the interparticle gaps or hotsites of the SERS active nanoassembly. In one embodiment, the analyte may be adsorbed by a dip and wash method of immersion.

The substrate is excited by an incident light source, as previously described. In a preferred embodiment, the incident light or radiation has a wavelength that excites surface plasmons of the SERS active nanoassembly, specifically the gold nanoparticles of the SERS active nanoassembly and within the substrate. In a preferred embodiment, these surface plasmons resonate in the interparticle gaps or hotsites with incident radiation is surface plasmon resonance (SPR). Analyte molecules in this enhanced EM field are subjected to stronger polarizing effects and thereby support Raman scattering with higher efficiency. In one embodiment, the substrate is excited by incident light in a manner such that the discrete gold nanoparticles have maximum electromagnetic near field distributions in the interparticle gaps in the range of 10-50 dBV/m, preferably 15-45 dBV/m, preferably 20-40 dBV/m, preferably 25-35 dBV/m, preferably 27-33 dBV/m, preferably 30-33 dBV/m.

For gold substrates, a laser wavelength operating in the range of 200-1100 nm allows efficient coupling to surface plasmons within the SERS active nanoassembly, preferably 300-1000 nm, preferably 400-900 nm, preferably 500-800 nm, preferably 500-700 nm, preferably 500-650 nm, preferably 600-650 nm. In a preferred embodiment, the laser exposure time is less than 5 s, preferably less than 4 s, preferably less than 3 s, preferably less than 2.5 s, preferably less than 2 s. In a preferred embodiment, the laser is operated at a power at the substrate surface of less than 10 mW, preferably less than 8 mW, preferably less than 6 mW, preferably less than 5 mW or 4 mW. These parameters allow for the minimization and avoidance of photodegradation.

In a preferred embodiment, the method of the present disclosure further comprises polarization of the incident light by any suitable manner, i.e. a half wave plate. In one embodiment, the incident light may be polarized at 0-180° relative to the plane of the long axis of the gold nanoparticles, preferably 30-150°, preferably 60-120°, preferably 90° corresponding to polarization along the plane of the long axis of the gold nanoparticles. In a preferred embodiment, the light source is polarizable and the Raman signal of the analyte is maximally enhanced when the light source is polarized along the plane of the long axis of the gold nanoparticles of the surface enhanced Raman scattering nanoassembly of the present disclosure. In a preferred embodiment, the light source is polarizable and the Raman signal of the analyte is minimally enhanced when the light source is polarized perpendicular to the plane of the long axis of the gold nanoparticles of the surface enhanced Raman scattering nanoassembly of the present disclosure (i.e. 0° or 180°).

In another embodiment, the method of the present disclosure further comprises polarization of the scattered Raman signal by any suitable manner, i.e. a rotary polarizer. In one embodiment, the scattered Raman signal may be polarized 0-180° relative to the plane of the long axis of the gold nanoparticles, preferably 0-150°, preferably 0-120°, preferably 0-90°, preferably 0-60°, preferably 0-30° relative to the plane of the long axis of the gold nanoparticles.

With regards to the fluorescence background, the SERS signal loses its enhancement at a higher background. In a preferred embodiment the light source is operated in a manner too weak to induce fluorescence from the analyte and the background fluorescence is largely due to the surface plasmon resonances in the gold nanoassembly. In a preferred embodiment, the light source is polarizable and the surface enhanced fluorescence signal of the analyte is maximally enhanced when the light source is polarized along the plane of the long axis of the gold nanoparticles of the surface enhanced Raman scattering nanoassembly of the present disclosure. In a preferred embodiment, the light source is polarizable and the fluorescence signal of the analyte is minimally enhanced when the light source is polarized perpendicular to the plane of the long axis of the gold nanoparticles of the surface enhanced Raman scattering nanoassembly of the present disclosure.

The scattered light or scattered Raman signal is detected and measured, as previously described. In a preferred embodiment the Raman signal is detected in the range of 200-2000 cm$^{-1}$, preferably 400-1800 cm$^{-1}$, preferably 600-1600 cm$^{-1}$, preferably 800-1400 cm$^{-1}$ depending on the analyte of interest. In a preferred embodiment the analyte has a Raman signal that is enhanced (with regards to atomic unit intensity) $10^2$-$10^{15}$ fold relative to the Raman signal of a substantially similar analyte measured by substantially similar method without the surface enhanced Raman scattering (SERS) active nanoassembly (i.e. on a bare glass layer), preferably, more preferably $10^4$-$10^{14}$, more preferably $10^5$-$10^{12}$, more preferably $10^6$-$10^{11}$, more preferably $10^7$-$10^{10}$. This level of enhancement should be sufficient for single molecule detection applications. In another embodiment, the method may further comprise correlating the scattered Raman signal from the analyte with a chemical structure of a known analyte, this may be done with the use of a computer.

According to a fourth aspect, the present disclosure relates to a method for producing the surface enhanced Raman scattering (SERS) nanoassembly of the present disclosure in any of its embodiments by wet chemistry techniques in a simple one step evaporation assisted method. The assembly of nanoparticles at liquid-liquid, liquid-air and liquid-solid interfaces is accomplished by the Langmuir-Blodgett technique, sedimentation or evaporation induced self-assembly and the adsorption of nanoparticles. The Langmuir-Blodgett technique has been used to form nanoparticle monolayers at the water-air interface and to transfer them onto a solid support. Close-packed 2D nanoparticle lattices and 1D arrays with varying surface density of nanoparticles were generated by tuning the wetting and the speed at which the substrate is withdrawn. In another embodiment, the hierarchical ordering of nanoparticles at the interface can be modulated by local heating of the monolayer of nanoparticles using, for example, irradiation.

Glass slides are washed with an alcohol in an ultrasonic bath for up to 2 hours, preferably up to 1 hour, preferably up to 45 min, preferably up to 30 min, preferably up to 20 min, preferably up to 15 min, preferably up to 10 min, preferably up to 5 min. In terms of the present disclosure, suitable alcohol solvents may include, but are not limited to, the short chain alcohols such as one or more of methanol, ethanol, propanol, isopropanol, butanol of the like. It is envisaged that the current method may be further adapted to use other polar protic solvents such as water or polar aprotic solvents such as acetone.

The washed glass slides are then immersed in a solution of colloidal gold comprising substantially spherical gold nanoparticles of 25-75 nm in diameter, preferably 30-70 nm, preferably 35-65 nm, preferably 40-60 nm, preferably 45-55 nm, or 50 nm in diameter. As used herein, a colloid is a substance in which microscopically dispersed insoluble particles are suspended throughout another substance.

In one embodiment, the colloidal suspension of gold nanoparticles has a mass concentration of less than 5.0 mg/mL, preferably less than 1.0 mg/mL, preferably less than 0.75 mg/mL, preferably less than 0.5 mg/mL, preferably less than 0.25 mg/mL, preferably less than 0.2 mg/mL, preferably less than 0.15 mg/mL, preferably less than 0.10 mg/mL, preferably less than 0.05 mg/mL, preferably less than 0.025 mg/mL. In one embodiment, the colloidal suspension has an atomic gold molarity of less than 10 mmol/L, preferably less than 5.0 mmol/L, preferably less than 2.0 mmol/L, preferably less than 1.0 mmol/L, preferably less than 0.75 mmol/L, preferably less than 0.5 mmol/L, preferably less than 0.4 mmol/L, preferably less than 0.3 mmol/L, preferably less than 0.2 mmol/L, preferably less than 0.1 mmol/L. In one embodiment, the colloidal suspension of the present disclosure has a particle concentration of $10^5$-$10^{15}$ particles/mL, preferably $10^6$-$10^{14}$, preferably $10^7$-$10^{13}$, preferably $10^8$-$10^{13}$, preferably $10^9$-$10^{13}$ particles/mL. In one embodiment, the colloidal suspension has a gold mass percentage by weight of less than 1%, preferably less than 0.5%, preferably less than 0.1%, preferably less than 0.05%, preferably less than 0.01%, preferably less than 0.005%.

In one embodiment, the washed glass slides are immersed in the colloidal gold solution at an inclination of 15-45° relative to the surface of the solution, preferably 20-40°, preferably 20-35°, preferably 25-30°, or an inclination of 30° relative to the surface of the solution. In one embodiment, excess ethanol helped in increasing the evaporation rate and preventing the pile up of nanoparticles at the meniscus. The convection flow of constituent gold nanoparticles toward the contact area was controlled by exposing the meniscus to air. As a result, the contact area turned into nanostructures in a random fashion. Based on the rate of the ethanol evaporation and transient changes in the local concentration of gold nanoparticles at the meniscus, different kinds of nanoassemblies were observed at different vicinities near contact area. The nanoassemblies were all confirmed to be monolayer rather than an agglomeration by atomic force micrscopy (AFM) and scanning electron microscopy (SEM).

In another embodiment, it is envisaged that the method to produce the surface enhanced Raman scattering (SERS) active nanoassembly of the present disclosure is not particularly limiting and may be adapted to incorporate a variety of methods that provide highly uniform and reproducible nanoassemblies in any of their embodiments including, but not limited to, techniques broadly categorized as ion implantation, wet chemistry, physical vapor deposition and mixtures thereof. In one embodiment, the SERS active nanoassembly may be fabricated by wet chemical methods involving the reduction of a SERS active metal salt (i.e. chloroauric acid or silver nitrate) with a reducing agent (i.e. sodium borohydride) and optionally in the presence of a colloidal stabilizer.

In one embodiment, the nanoassembly may be formed by lithography, more preferably nanolithography. Nanolithography techniques may be categorized as in serial or parallel, mask or maskless/direct-write, top-down or bottom-up, beam or tip-based, resist-based or resist-less methods all of which are acceptable in terms of the present disclosure. Exemplary nanolithography techniques include, but are not limited to, optical lithography, photolithography, directed self-assembly, extreme ultraviolet lithography, electron beam lithography, electron beam direct write lithography, multiple electron beam lithography, nanoimprint lithography, step-and-flash imprint lithography, multiphoton lithography, scanning probe lithography, dip-pen nanolithography, thermochemical nanolithography, therman scanning probe lithography, local oxidation nanolithography, molecular self-assembly, stencil lithography, X-ray lithography, laser printing of single nanoparticles, magnetolithography, nanosphere lithography, proton beam writing, charged particle lithography, ion projection lithography, electron projection lithography, neutral particle lithography and mixtures thereof.

The examples below are intended to further illustrate protocols for preparing and characterizing the surface enhanced Raman scattering (SERS) active nanoassembly of the present disclosure. Further, they are intended to illustrate assessing the properties of these nanoassemblies. They are not intended to limit the scope of the claims.

Example 1

Preparation of the Surface Enhanced Raman Scattering (SERS) Active Nanoassembly

Colloidal gold nanoparticles (50 nm in diameter) were received from BBlnternational (Cardiff, UK) and used without further modification. A simple and modified strategy was adopted to fabricate the anisotropic nanoassembly. Colloidal gold nanoparticles were immobilized on a glass substrate without any surfactant or capping reagent. In the self-assembly technique, surfactants or capping reagents act as a mesh for the adhesion of nanoparticles into close packed structure, and thus, the network is converted into a self-assembled nanostructure. However, for SERS applications, residual surfactants may prevent the Raman dye molecules from coming close to the center of the interstitials. In addition, surfactants induce a huge background emission, which is unfavorable for the specific detection of analytes [K. E. Shafer-Peltier, C. L. Haynes, M. R. Glucksberg and R. P. VanDuyne, J. Am. Chem. Soc., 2003, 125, 588-593.—incorporated herein by reference in its entirety].

The gold nanoassembly was prepared in a simple one step process. Glass slides were washed with ethanol in an ultrasonic bath for 15 min and then immersed at ~30° inclination in an ethanolic solution of colloidal gold. Excess ethanol helped in increasing the evaporation rate and preventing the pile up of nanoparticles at the meniscus. The convection flow of constituent gold nanoparticles toward the contact area was controlled by exposing the meniscus to air. As a result, the contact area turned into nanostructures in a random fashion. Based on the rate of ethanol evaporation and transient changes in the local concentration of gold nanoparticles at the meniscus, different kinds of nanoassemblies were observed at different vicinities near the contact area.

Example 2

Surface Enhanced Raman Scattering (SERS) Experimental Setup

The anisotropic nanoassemblies under investigation were found to be SERS active. Crystal Violet (CV, $C_{25}H_{30}Cl\,N_3$, Wako Pure Chemical Industries Ltd.) molecules were adsorbed to monitor the SERS activity. The prepared nanoassemblies were dipped in a 1 µM solution of CV for 15 min and washed with pure water. It was assumed that only a monolayer of CV remained at the surface, since the interaction between the gold nanoparticles and the CV molecules is stronger than that amongst the CV molecules.

The SERS measurements were performed using a 647 nm laser from a $Kr^+$ source [T. Itoh, K. Hashimoto and Y. Ozaki, Appl. Phys. Lett., 2003, 83, 2274-2276.—incorporated herein by reference in its entirety]. The exposure time for SERS imaging was set to 2 s under less than 4 mW of laser power (density, ~50.93 W $cm^{-2}$) at the sample surface in order to avoid photodegradation. Surface plasmon resonance (SPR) and SERS images were captured at the same spatial position with a slight variation in the optical path. Hence, it is reasonable to consider that the interstitials remain unchanged for a particular scattering volume under irradiation.

A high resolution charge-coupled detector (CCD, Hamamatsu photonics ORCA® AG) was attached to the microscope for acquiring SPR and SERS images. The scattering signal was collected through an objective lens (60×, NA: 0.7) and detected by using a combination of a CCD camera and a polychromator. A half wave plate was inserted in the optical path of the laser beam to investigate polarization dependent SERS characteristics at the same position. Between two measurements, the laser was blocked to avoid any unexpected irradiation effect on the sample, although the incident power was kept very low. A rotary polarizer was place in the optical path of the scattered signal to investigate polarization selective SERS characteristics at the same position.

Example 3

Atomic Force Microscopy (AFM) and Scanning Electron Microscopy (SEM) Analysis of the Prepared Surface Enhanced Raman Scattering (SERS) Active Nanoassembly The nanoassemblies were confirmed to be a monolayer rather than an agglomeration by atomic force microscopy (AFM) and scanning electron microscopy (SEM). Atomic force microscopy (AFM) observations confirmed that the prepared anisotropic gold nanoassembly is several tens of micrometers long. A typical AFM image is shown in FIG. 1. A close observation by scanning electron microscopy (SEM), as shown in FIG. 2A, confirmed that the constituent gold nanoparticles were neither in physical contact nor agglomerated, but separated by small interparticle gaps (2-5 nm). As per the hotsite mechanism, such a small interparticle gap is essential for giant SERS enhancement. The EM field is assumed to be localized and substantially enhanced at such interstitials, and thus, giant enhancement in the SERS is expected.

Example 4

Figure 3:
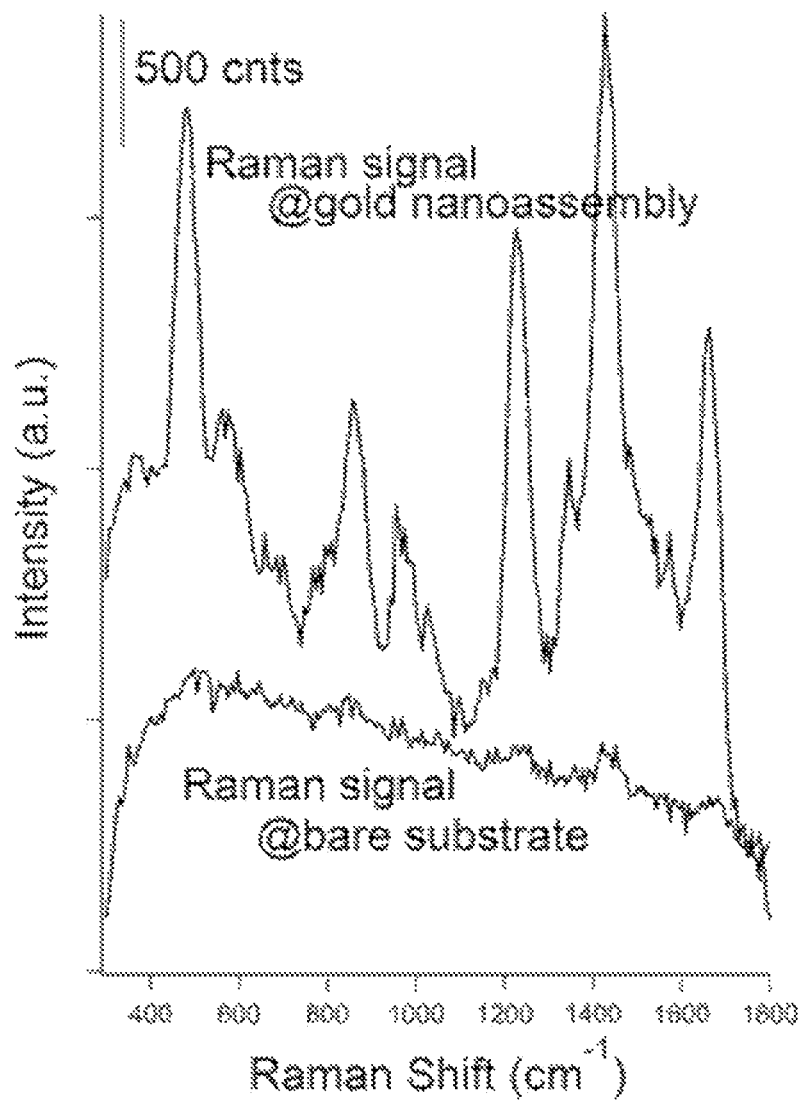
FIG. 3 is a SERS spectrum of crystal violet (CV) dye adsorbed on the prepared SERS active nanoassembly and a SERS spectrum of crystal violet (CV) dye on a bare glass substrate without the SERS active nanoassembly.

Surface Enhanced Raman Scattering (SERS) and Surface Plasmon Resonance (SPR) Analysis of the Prepared SERS Active Nanoassembly Indeed, a strong enhancement in the SERS signal of the Crystal Violet (CV, $C_{25}H_{30}ClN_3$) was observed in the presence of the gold nanoassembly. FIG. 3 shows the Raman signal of CV adsorbed on the gold nanoassembly and that on a bare glass substrate. The SERS peaks obtained in these experiments coincide with those reported by theoretical and experimental investigations [M. V. Canamares, C. Chenal, R. L. Birke and J. R. Lombardi, *J. Phys. Chem. C*, 2008, 112, 20295-20300.; and S. L. Kleinman, E. Ringe, N. Valley, K. L. Wustholz, E. Phillips, K. A. Scheidt, G. C. Schatz and R. P. VanDuyne, *J. Am. Chem. Soc.*, 2011, 133, 4115-4122.— each incorporated herein by reference in its entirety]. Clearly, the Raman signal in the presence of the gold nanoassembly was enhanced by several orders of magnitude compared to that obtained on the bare substrate. The negligible Raman signal observed on the bare substrate could be because of sneaking or stray scattering from neighboring nanoparticles. The scattering volume under investigation was kept at 2 μm×2 μm; therefore, it is likely to have a fraction of stray signals from neighboring SERS-active spots.

Figure 4A:
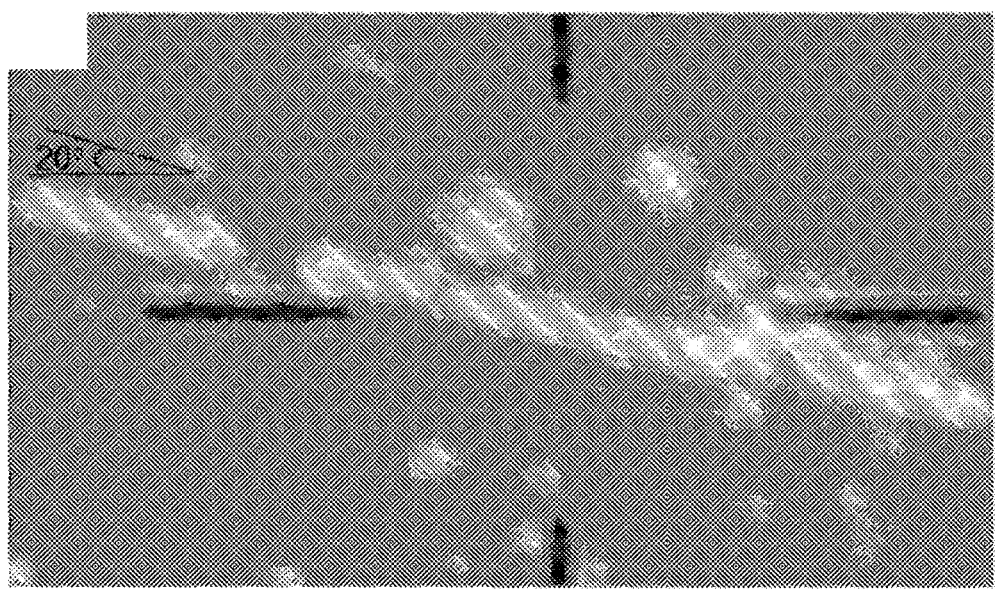
FIG. 4A is a surface plasmon resonance (SPR) image of the prepared SERS active nanoassembly of 50 nm gold nanoparticles captured by a high resolution charge-coupled detector (CCD) camera.

Dark-field microscopic measurements were carried out using a combination of a dark-field condenser and a white light source [J. Nelayah, O. Stephan, M. Kociak, F. J Garcia de Abajo, L. Henrard, I. Pastoriza-Santos, L. M. Liz-Marzán and C. Colliex, *Microsc. Microanal.*, 2007, 13, 144-145.— incorporated herein by reference in its entirety]. FIG. 4A shows a dark-field microscopic image of the anisotropic assembly of 50 nm gold nanoparticles. This image reflects localized surface plasmon resonance (SPR) excitations on the substrate. Inhomogeneous intensity distribution was observed from segment to segment of the assembly in the SPR image. The overall topographic observations confirmed that the gold nanoparticles remain assembled as two-dimensional structures rather than as agglomerations, even after the analyte adsorption. The anisotropic gold nanoassembly was found to be tilted ~20° to the horizontal axis, as indicated in FIG. 4A.

Figure 4B:
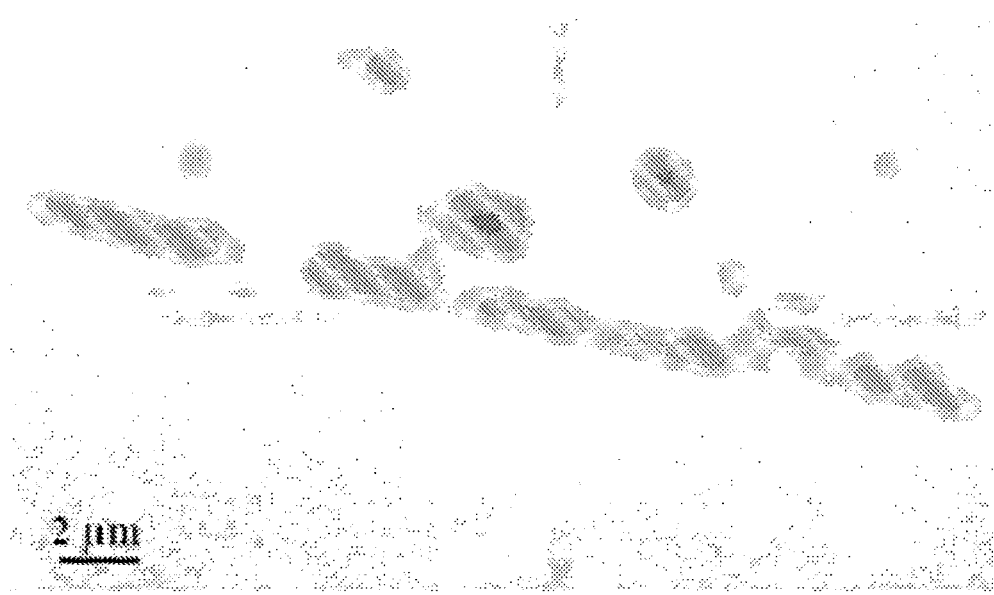
FIG. 4B is a SERS image of the SERS active nanoassembly of 50 nm gold nanoparticles captured by a high resolution CCD camera of the same sample at the same position as the SPR image of the prepared SERS active nanoassembly of 50 nm gold nanoparticles.

Since SERS is related to the SPR-mediated localized EM field, the same sample was used for far-field Raman measurements in the same platform, with just a slight variation in the optical set up. FIG. 4B shows a SERS image of the same gold assembly adsorbed with CV as shown in FIG. 4A. The SERS signals were found to be strongly enhanced and inhomogeneously distributed along the assembly. It is noted that such a SERS image essentially corresponds to cumulative SERS photons combined with background fluorescence emission. Moreover, Rayleigh leakage or interactions from the laser itself can interfere with the image [Z. Xie, Y. Lu, H. Wei, J. Yan, P. Wang and H. Ming, *Appl. Phys. B*, 2009, 95, 751-755.—incorporated herein by reference in its entirety]. Hence, the spectral analysis is more reliable than the apparent imaging by the charge-coupled detector (CCD) camera, as discussed below.

Figure 5A:
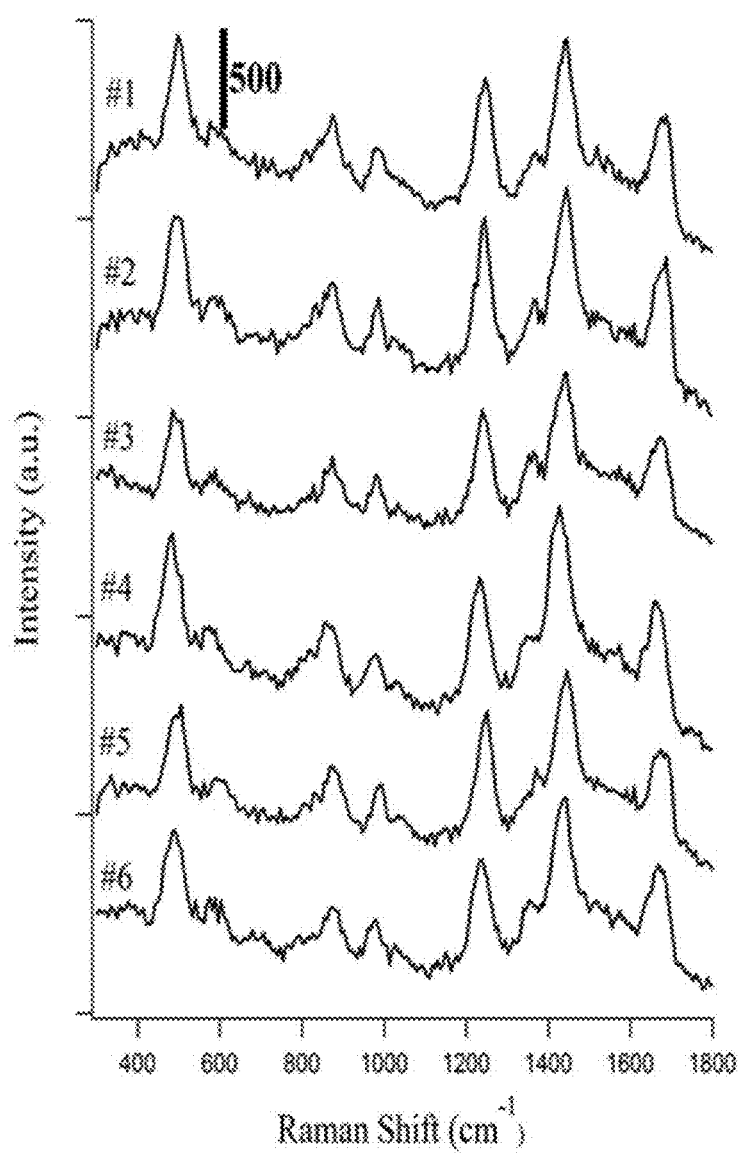
FIG. 5A is a SERS spectra of CV adsorbed onto different segments (#1-#6) of the prepared SERS active nanoassembly.
Figure 5B:
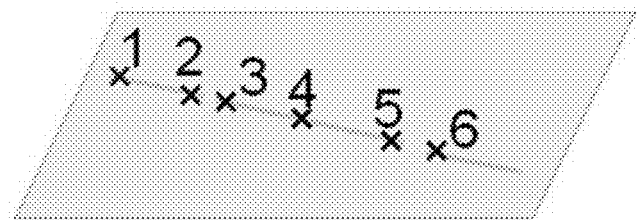
FIG. 5B is a free hand schematic illustrating the positioning of the different segments (#1-#6) of the prepared SERS active nanoassembly.
Figure 5C:
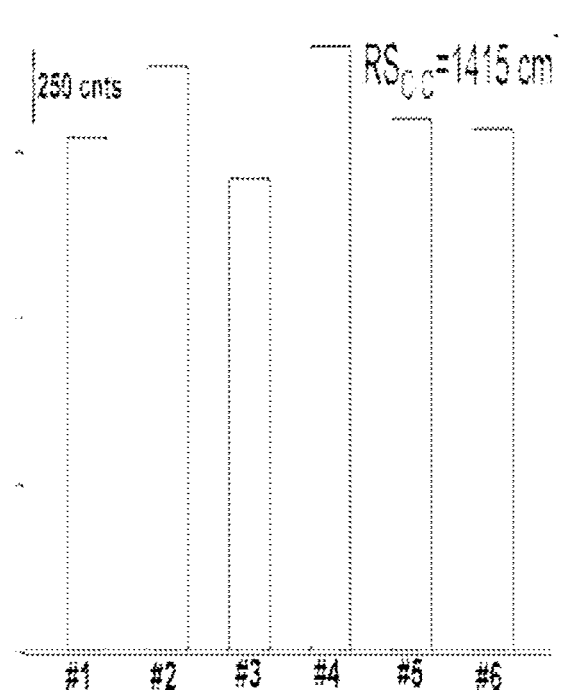
FIG. 5C illustrates the SERS intensity of the 1413 cm$^{-1}$ band of CV obtained at different segments (#1-#6) of the prepared SERS active nanoassembly.

FIG. 5A shows a series of SERS spectra obtained at different positions marked 1 to 6, as shown in FIG. 5B. FIG. 5B represents a free hand drawing similar to that of the object undertaken in the present disclosure. Inhomogeneous intensity distribution in the SERS image was observed from segment to segment. The Raman intensities of the 1413 cm-1 SERS band of CV (i.e., the C—C bending mode) obtained at different segments are depicted as bar graphs in FIG. 5C. Strong and nearly similar signal enhancements are seen at different positions, except at positions 2 and 4, wherein the signal enhancement is relatively higher (by ~100 cnts). Ensemble SERS measurements by far-field configuration average all the enhanced signals from the total scattering volume (in this case, 2 μm×2 μm on a planar surface). Hence, the segment within this area consists of many sites, with only some of them being active [M. K. Hossain, T. Shimada, M. Kitajima, K. Imura and H. Okamoto, Langmuir, 2008, 24, 9241-9244.—incorporated herein by reference in its entirety].

Example 5

Polarization Dependent Surface Enhanced Raman Scattering (SERS) Analysis of the Prepared Nanoassembly In the case of dimers or trimers, a strong SERS signal can be realized by tuning the laser polarization, whereas in ensemble SERS measurements, the scenario is more complicated. In long range structures, an individual particle is surrounded by many others, and the local EM field is affected accordingly. As a result, polarization dependent and polarization selective SERS characteristics for a long range specimen cannot be explained by the EM mechanism alone [M. Moskovits, *Rev. Mod. Phys.*, 1985, 57, 783-826.— incorporated herein by reference in its entirety]. Hence, the elongated gold nanoassembly with limited interstitials used in the current work is possibly a good candidate for this purpose.

Figure 6A:
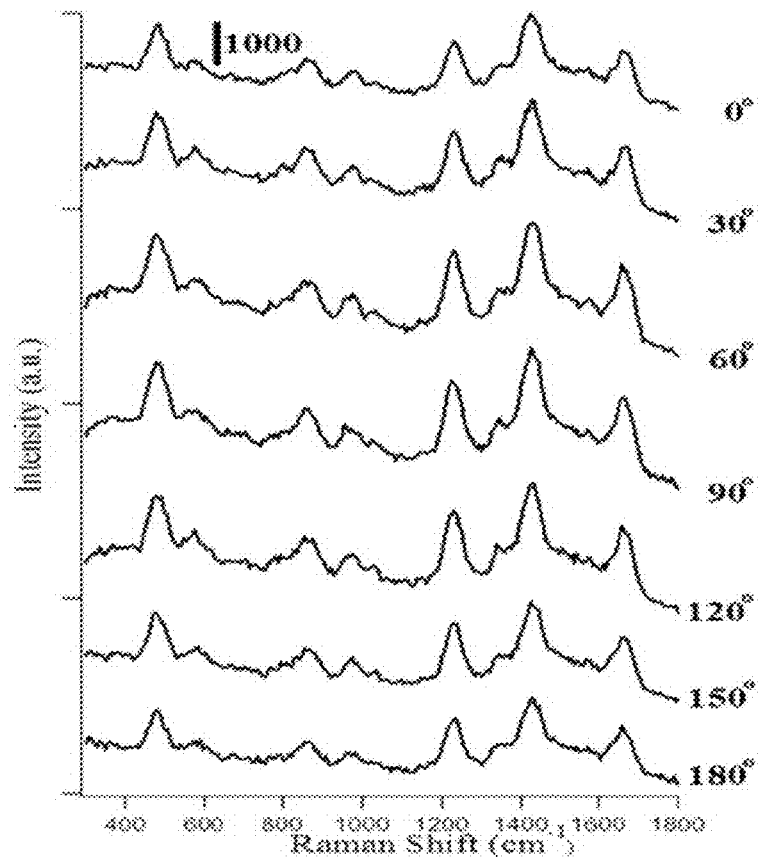
FIG. 6A is a polarization dependent SERS spectra of CV adsorbed on the prepared SERS active nanoassembly obtained at segment #4 with incident polarization varying from 0° to 180° with an interval of 30° and the vertical bar representing the photon intensity.
Figure 6B:
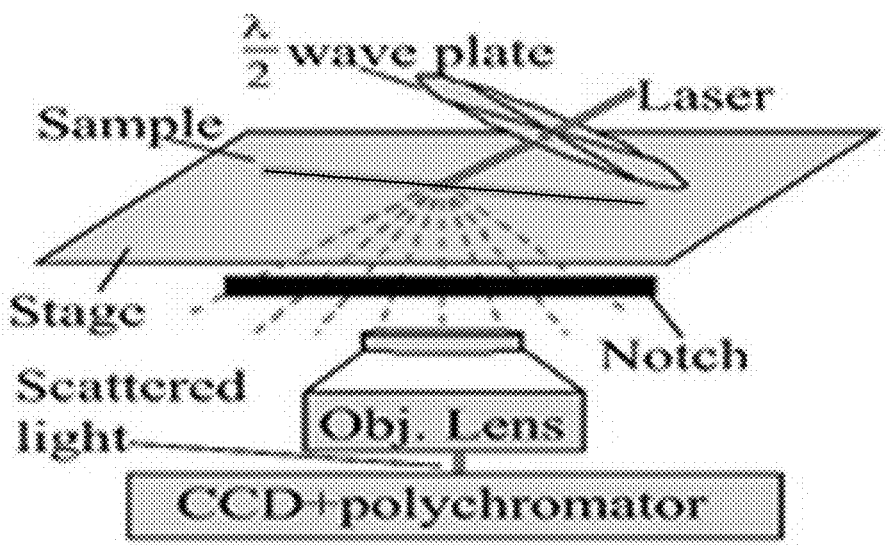
FIG. 6B is a schematic diagram of the polarization dependent SERS experimental setup.
Figure 6C:
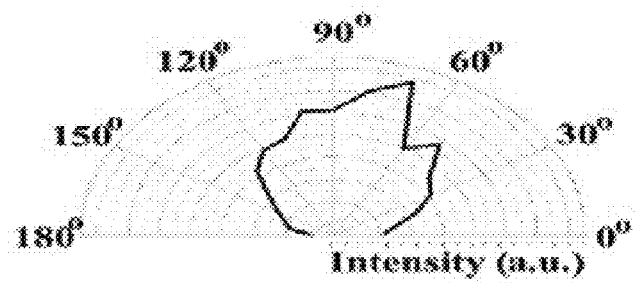
FIG. 6C is a half polar graph of the C—C bending mode of CV (1413 cm$^{-1}$) at an interval of 10° of incident polarization.

FIG. 6A shows a series of polarization dependent SERS spectra obtained at a specific position (position #4 shown in FIG. 5B) with different incident polarization angles. The positin marked #4 is chosen because of the stronger SERS enhancement. The experimental configuration is schematically depicted in FIG. 6B, where the incident laser is polarized using a half wave plate and the scattering signal is collected by the objective lens positioned behind the stage; thus, the substrate is left untouched for the entire series of experiments. FIG. 6C represents the half polar graph for the 1413 cm-1 SERS band of CV (i.e., the C—C bending mode) obtained at an interval of 10° of the incident polarization.

In polarization dependent measurements, the peak intensity changed gradually and reached the highest value at an angle of 70°. From the topographic measurements, it was found that the anisotropic nanoassembly is tilted by ~20° from the horizontal axis. Hence at 70° polarization, the incident laser beam coincides with the long axis of the nanoassembly. A plausible reason for this is described below with reference to the localized EM field distribution at various incident polarizations.

In simple nanoparticle dimers, giant enhancement in SERS can be obtained due to localized EM field at interstitials that are known as "hotsites". When the proximity between two nanoparticles becomes very close, the optical field at interstitials reaches its highest. The phenomenon is termed the "EM enhancement factor" which is usually considered to be proportional to the fourth power of the ratio between the local electric field and the incident field. Extensive theoretical studies have been reported [P. K. Aravind and H. Metiu, *J. Phys. Chem.*, 1982, 86, 5076-5084.; and J. P. Kottmann, O. J. F. Martin, D. R. Smith and S. Schultz, *Phys. Rev. B*, 2001, 64, 235402-1-235402-10.—each incorporated herein by reference in its entirety]. On the other hand, for an aggregate of many nanoparticles, the hotsites become unpredicted and usually occur due to symmetry breaking [K. Kneipp, Y. Wang, H. Kneipp, I. Itzkan, R. R. Dosari and M. S. Feld, *Phys. Rev. Lett.*, 1996, 76, 2444-2447.~incorporated herein by reference in its entirety]. In addition, it has been reported that neighboring hotsites always tend to have coalescence and hybridization through intense energy percolation [M. K. Hossain, T. Shimada, M. Kitajima, K. Imura and H. Okamoto, *J. Micros.*, 2008, 229, 327-330.—incorporated herein by reference in its entirety].

This was the main motivation to choose a suitable specimen that lay in between single dimer and large nanoaggregates. The nanoassembly under investigation was an interstitials limited SERS active substrate. In such an assembly, a single hotsite occurring at polarization across the long axis was expected to be undisturbed in an ideal case, whereas all the interstitials along the long axis will be active at in plane polarization. A theoretical validation was also carried out and is explained below.

Example 6

Polarization Selective Surface Enhanced Raman Scattering (SERS) Analysis of the Prepared Nanoassembly It is well established that the SERS enhancement depends on incident polarization direction. Stronger SERS enhancement appears for parallel polarization with reference to the interparticle axis and vice versa. However, the polarization selective SERS signal is not so straight forward, because of unknown adsorption orientation of molecules and nanoscale topography of the underlying substrate. According to the two fold EM enhancement mechanism, the scattering signal interacts with the localized plasmons and is modulated. Since a localized EM field is incident polarization specific, polarization selective SERS characteristics should reflect the scattering signal and SPRs excitation. A uniform enhancement in polarization selective SERS measurements was observed.

Figure 7A:
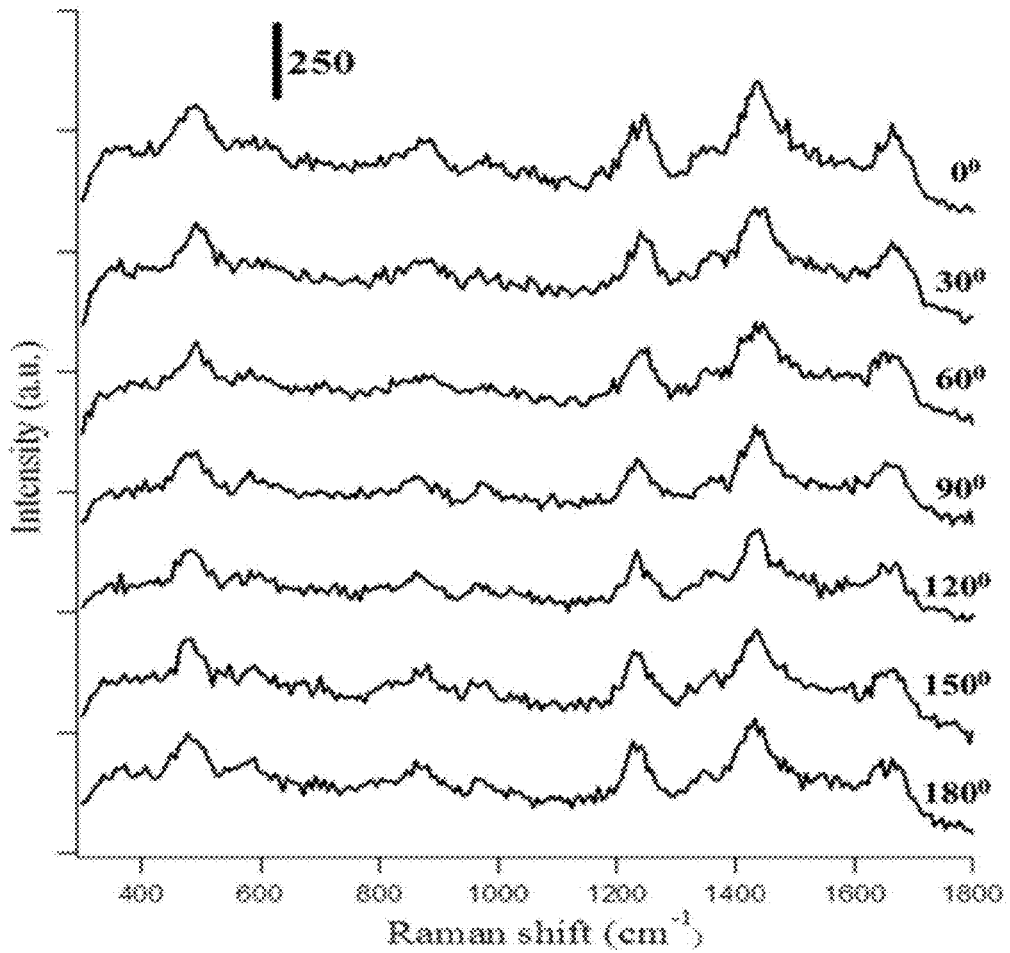
FIG. 7A is a polarization selective SERS spectra of CV adsorbed on the prepared SERS active nanoassembly obtained at segment #4 with fixed incident polarization while a rotary polarizer is varied from 0° to 180° with an interval of 30°.
Figure 7B:
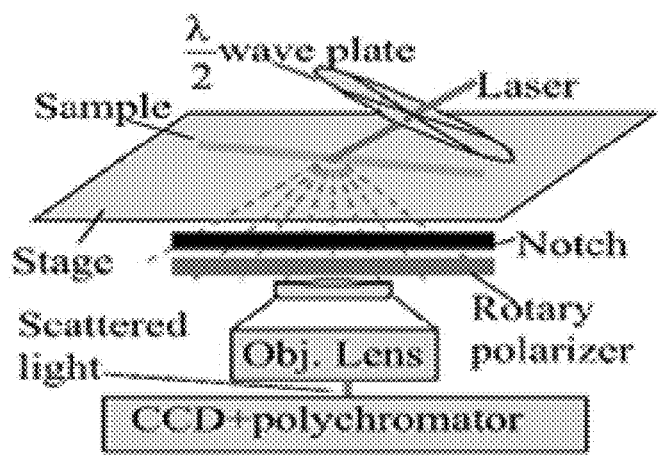
FIG. 7B is a schematic diagram of the polarization selective SERS experimental setup.
Figure 7C:
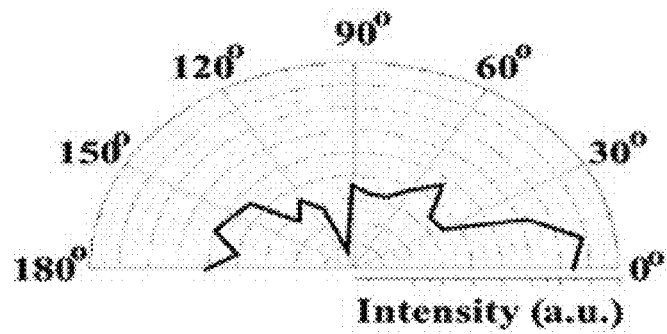
FIG. 7C is a half polar graph of the C—C bending mode of CV (1413 cm$^{-1}$) at an interval of 10° of rotary polarizer.

FIG. 7A shows a series of polarization selective SERS spectra recorded at the same position (position #4 showed in FIG. 5B). The position #4 is chosen because of the stronger SERS enhancement and for comparison with polarization dependent SERS. The experimental configuration is schematically depicted in FIG. 7B, where the incident laser polarization is unchanged and the scattering signal is passed through the rotary polarizer and collected by the objective lens before the spectrometer. FIG. 7C represents the half polar graph for the 1413 $cm^{-1}$ band of CV obtained at an interval of 10° of polarization. It is noteworthy that the polarization selective peak intensity remains more or less unchanged at a particular incident polarization.

Example 7

Fluorescence Analysis of the Prepared Surface Enhanced Raman Scattering (SERS) Active Nanoassembly Regarding the fluorescence background, the SERS signal loses its enhancement at a higher background and vice versa [M. K. Hossain, G. G. Huang, T. Kaneko and Y. Ozaki, *Phys. Chem. Chem. Phys.*, 2009, 11, 7484-7490.—incorporated herein by reference in its entirety]. Two factors must be considered for fluorescence background emission at a specific adsorption of an analyte to the substrate: i) the excitation laser itself and ii) the SPR excitation from the underlying substrate. The excitation wavelength of 647.2 nm from the $Kr^+$ laser is too weak to induce fluorescence from CV. Hence, the background emission is mainly due to SPR excitation in the gold nanoassembly. The SPR image shown in FIG. 4A represents an inhomogeneous distribution of SPR excitations along the assembly. It has been shown that several SPR excitations are possible in elongated and long range colloidal gold nanostructures [M. K. Hossain, Y. Kitahama, G. G. Huang, T. Kaneko and Y. Ozaki, *Appl. Phys. B*, 2008, 93, 165-170.—incorporated herein by reference in its entirety]. At position #4, weak fluorescence background emissions were recorded, as mentioned previously. Although the excitation intensity is too weak to induce fluorescence in this case, incident polarization dependent fluorescence emissions were observed for the elongated gold nanoassembly. In fact, fluorescence emission enhancement resulted from the SPR mediated local EM field at the interstitials.

Figure 8A:
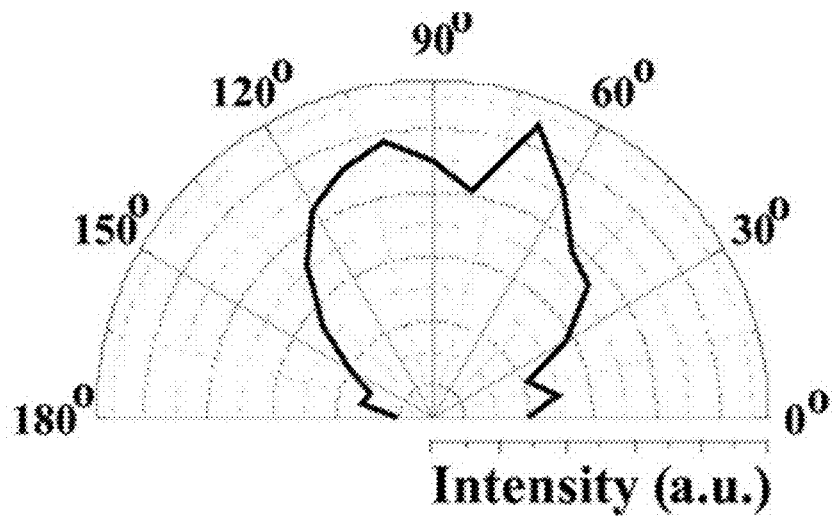
FIG. 8A is a half polar graph of polarization dependent fluorescence emission obtained at an interval of 10° of incident polarization.
Figure 8B:
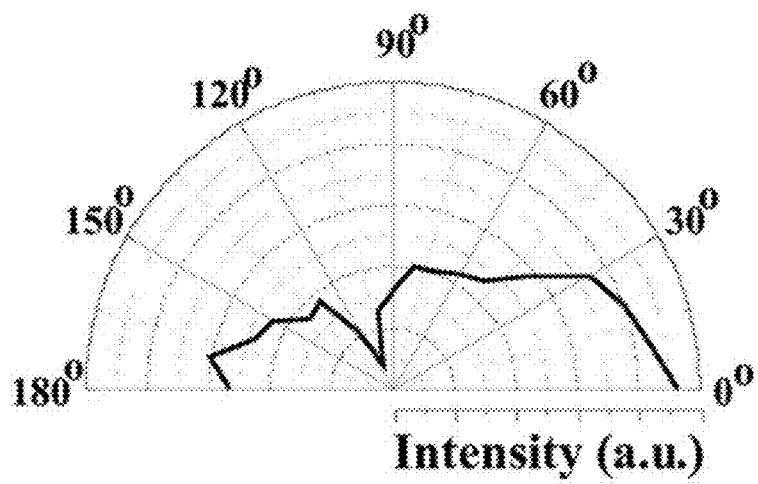
FIG. 8B is a half polar graph of polarization selective fluorescence emission obtained at an interval of 10° of rotary polarizer and obtained at the same position as the half polar graph of polarization dependent fluorescence emission.

FIG. 8A presents the half polar graph of fluorescence emission obtained at an interval of 10° incident polarization. It is noteworthy that the intensity reaches the highest value at an angle of 70°, similar to the case of polarization dependent SERS. Since the anisotropic assembly is tilted by ~20°, at 70° polarization, the incident laser beam coincides with the long axis of the nanoassembly. On the other hand, uniform fluorescence emission on average was observed in the polarization selective measurements, as shown in FIG. 8B. According to surface enhanced fluorescence (SEF), the fluorescence intensity depends on the position of the molecule from the surface and the intensity of the localized EM field mediated by SPR. In the case of a dry sample, any variation in the molecule's position is discarded, and localized EM field distribution can be manipulated by incident polarization. Hence, similar to SERS, fluorescence emission is enhanced at a stronger EM field and vice versa. It is well understood that in-plane polarization to the interparticle axis introduces the highest localized EM field at the interstitial. On the other hand, in the case of polarization selective SERS measurements, the incident polarization is kept unchanged and the scattering signal is filtered by a rotary polarizer. Since there is no variation in the localized EM field distribution (because of fixed incident polarization), the fluorescence background emission remains approximately uniform, as observed in FIG. 8B. The observations can be demonstrated through the two fold EM field enhancement mechanism.

Example 8

Three-Dimensional (3D) Finite-Difference Time-Domain (FDTD) Analysis

The giant SERS enhancement, which is typically on the order of $10^8$-$10^{10}$, has been mentioned earlier and can be explained by a two-fold EM field enhancement mechanism [B. Pettinger, *J. Chem. Phys.*, 1986, 85, 7442-7451.; and T. Itoh, K. Yoshida, V. Biju, Y. Kikkawa, M. Ishikawa and Y. Ozaki, *Phys. Rev. B*, 2007, 76, 085405-1-085405-5.—each incorporated herein by reference in its entirety]. A quantum mechanical approach for surface enhanced optical processes summarizing two-fold enhancements was first reported where two main interactions are responsible: i) incident photon SPR interaction and scattered photon SPR interaction. Since the incident photon is much stronger than the scattered one, the first interaction is predominant. In other words, the incident photon energy irradiated on the adsorbent is scattered from an adsorbate because of SPR mediated dipole-dipole interactions. In addition, the scattered photon from the molecules resonates with the plasmon, as its wavelength is close to that of the incident photon. The EM field is further enhanced and thus, cumulative strong Raman scattering light is emitted. Hence, the total enhancement factor, M, is given by formula (II):

$$M = \left|\frac{E^{LOC}(\lambda_L)}{E^I(\lambda_L)}\right|^2 \times \left|\frac{E^{LOC}(\lambda_L \pm \lambda_R)}{E^I(\lambda_L \pm \lambda_R)}\right|^2 = M_1(\lambda_L) \times M_2(\lambda_L \pm \lambda_R) \quad (II)$$

In formula (I), M is the total enhancement factor and $E^I$ and $E^{Loc}$ are the amplitudes of the incident and local electronic fields, respectively; $\lambda_L$ is the excitation wavelength; $+\lambda_R$ and $-\lambda_R$ are the wavelengths of the anti-Stokes and Stokes Raman shifts, respectively; and $M_1$ and $M_2$ are the first and second enhancement factors, respectively.

As noted above, the EM distribution at the interstitial sites strongly depends on the incident polarization. The highest confinement is observed when the incident polarization is parallel to the interparticle axis, and thus, the SERS and SEF enhancement under these conditions is the highest. On the contrary, the lowest enhancement is observed with the incident polarization normal to the interparticle axis. A three-dimensional (3D) FDTD analysis, with the same parameters used under the experimental conditions ($\lambda_{exc}$=647 nm, $D_{Au}$=50 nm, Gap=2 nm), was carried out to understand the observations.

Figure 9A:
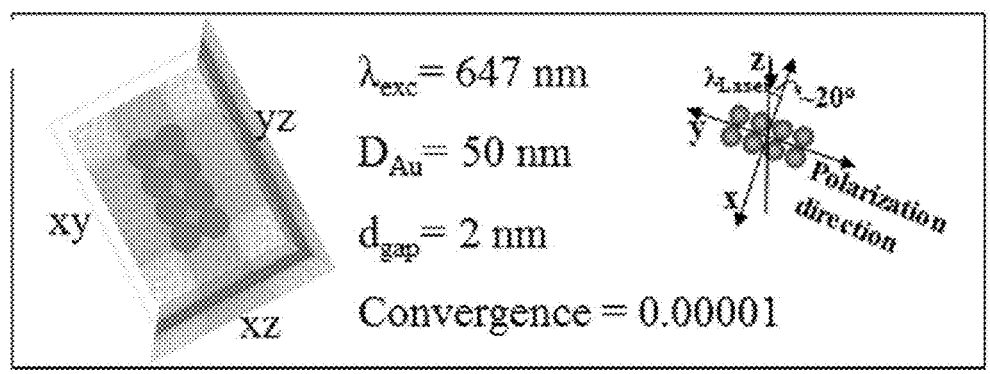
FIG. 9A is the mesh, parameters and laser configuration ($\lambda_{exc}$=647 nm, $D_{AU}$=50 nm, $d_{gap}$=2 nm) adopted. The bar shows the field intensity and one headed arrows demonstrate the respective incident polarizations.
Figure 9B:
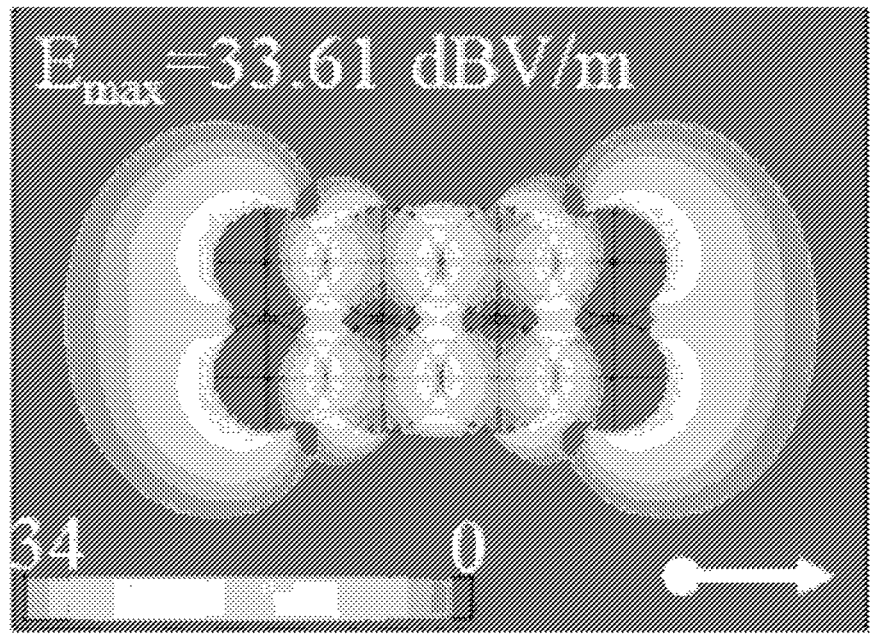
FIG. 9B is an EM near field distribution of gold nanoparticles meshed anisotropically in two rows at 0° polarization relative to the long axis and the corresponding $E_{max}$=33.61 dBV/m.
Figure 9C:
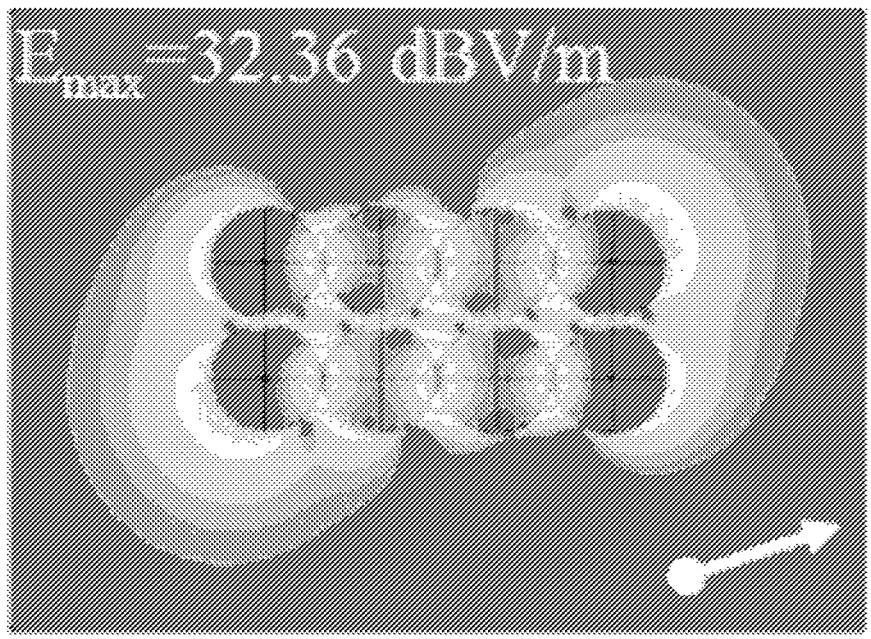
FIG. 9C is an EM near field distribution of gold nanoparticles meshed anisotropically in two rows at 30° polarization relative to the long axis and the corresponding $E_{max}$=32.36 dBV/m.
Figure 9D:
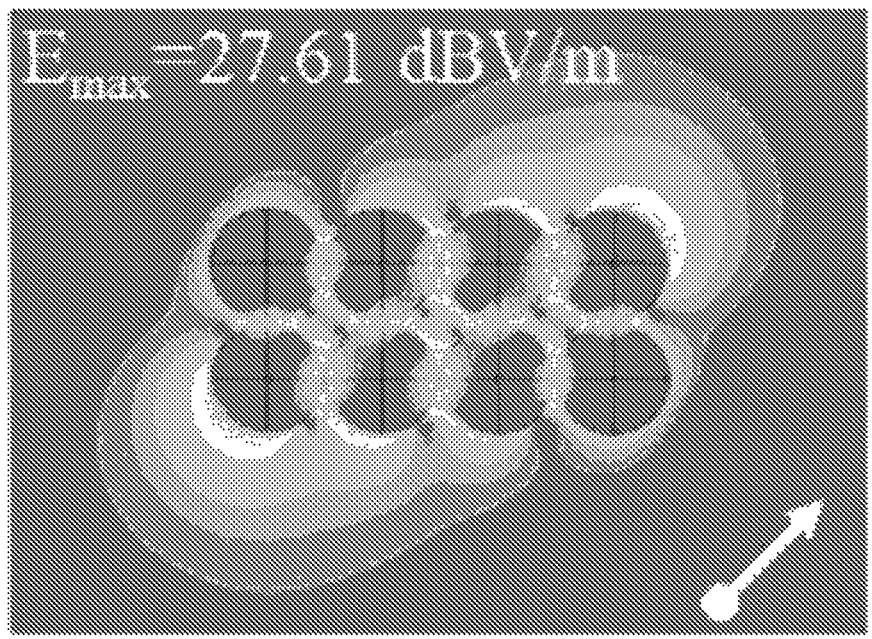
FIG. 9D is an EM near field distribution of gold nanoparticles meshed anisotropically in two rows at 60° polarization relative to the long axis and the corresponding $E_{max}$=27.61 dBV/m.
Figure 9E:
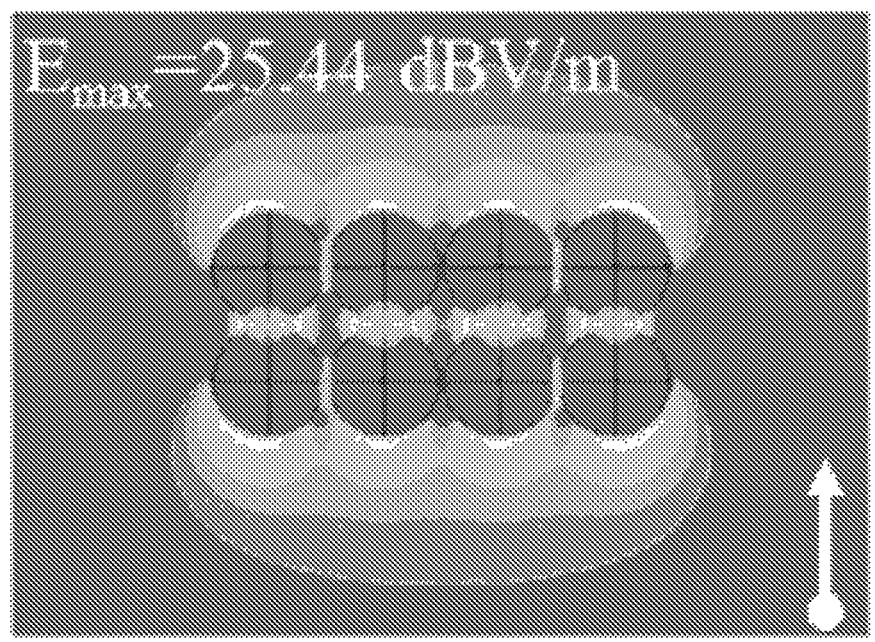
FIG. 9E is an EM near field distribution of gold nanoparticles meshed anisotropically in two rows at 90° polarization relative to the long axis and the corresponding $E_{max}$=25.44 dBV/m.
Figure 9F:
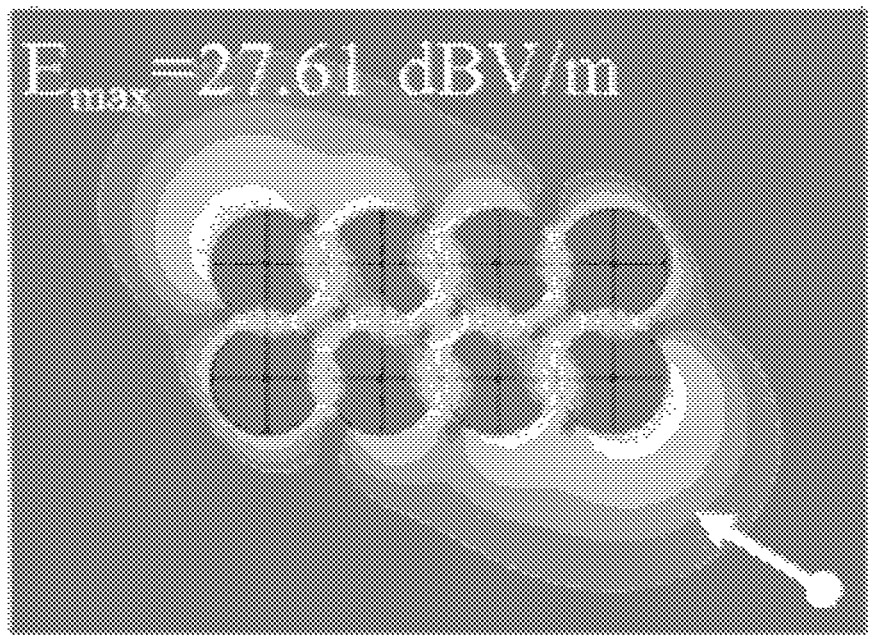
FIG. 9F is an EM near field distribution of gold nanoparticles meshed anisotropically in two rows at 120° polarization relative to the long axis and the corresponding $E_{max}$=27.61 dBV/m.
Figure 9G:
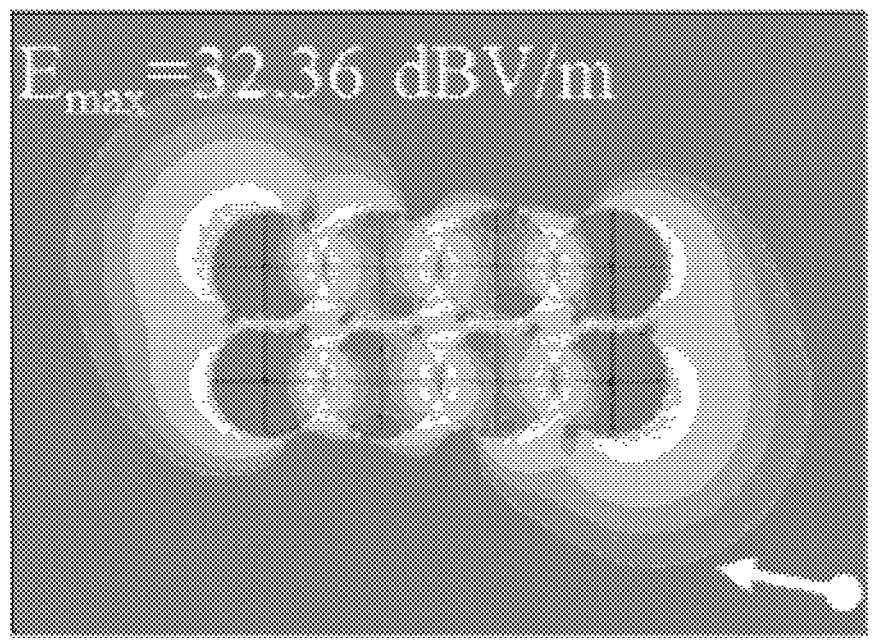
FIG. 9G is an EM near field distribution of gold nanoparticles meshed anisotropically in two rows at 150° polarization relative to the long axis and the corresponding $E_{max}$=32.36 dBV/m.
Figure 9H:
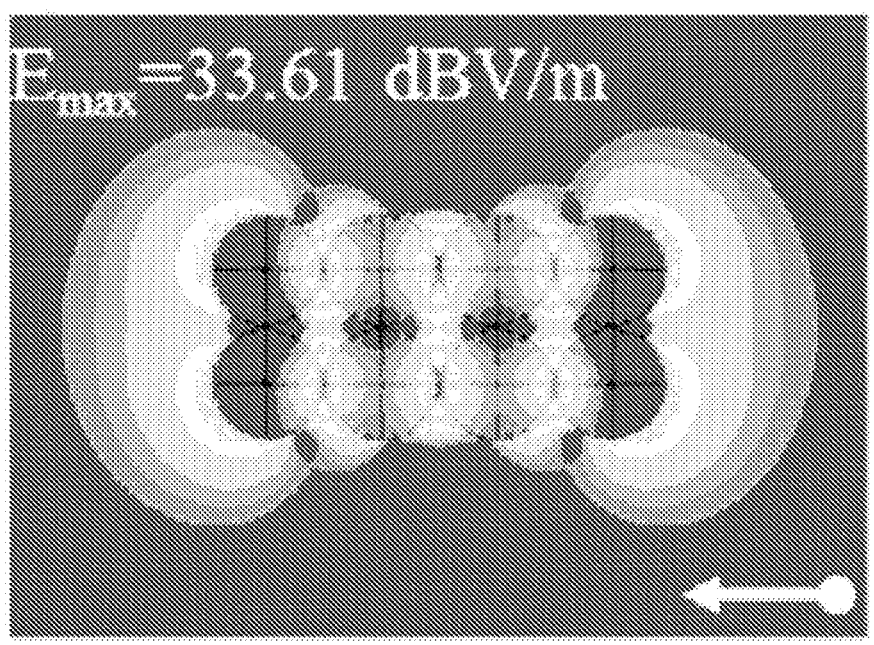
FIG. 9H is an EM near field distribution of gold nanoparticles meshed anisotropically in two rows at 180° polarization relative to the long axis and the corresponding $E_{max}$=33.61 dBV/m.

The incident laser polarization was tuned to observe the EM field distribution, since the SERS and SEF enhancement in this particular case was found to be dependent on the incident laser polarization. For the theoretical calculations to be relevant to the experimental measurements, eight nano-objects were inserted into the mesh in two rows, so that collective EM field distribution could be realized. In such a configuration, 10 interstitials are obtained, 6 sites are supposed to be the strongest at in-plane polarization to the long axis and the remaining 4 sites are the strongest at out-of-plane polarization. The mesh, parameters, and laser configuration are shown in FIG. 9A. FIG. 9B, FIG. 9C, FIG. 9D, FIG. 9E, FIG. 9F, FIG. 9G, and FIG. 9H show the near-field distribution from 0° to 180° incident polarization, at intervals of 30°. The intensity bar in FIG. 9B represents the intensity scale for all images.

For in-plane polarization to the long interparticle axis (i.e., 0° and 180° polarization), the strongest EM near-field distributions, with $E_{max}$=33.61 dBV/m, were found to occur at the six interstitials along the the horizontal axis (FIG. 7B and FIG. 7H). The EM near-field distribution for the other sites along the vertical axis was negligible. In such a scenario, the SERS and SEF signals from the analyte of interest should show the highest enhancement. For orthogonal polarization (90° polarization), the weakest EM near-field distributions, with $E_{max}$=25.44 dBV/m, were observed at the four interstitials along the vertical axis, as shown in FIG. 7E. For 30° (FIG. 7C and FIG. 7G) and 60° (FIG. 7D and FIG. 7E) polarization, the EM near-field intensity was 32.36 dBV/m and 27.61 dBV/m, respectively. Hence, in the case of orthogonal polarization, the SERS and SEF signals from the analyte of interest should show minimum enhancement.

Indeed, a similar trend was observed in this investigation. As explained in FIG. 6C and FIG. 8A, a strong SERS signal for the 1413 cm-1 band of CV and fluorescence background emission were recorded at 70° incident polarization. Since the gold nanoassembly is tilted by ~20° from the horizontal axis, 70° polarization of the incident laser becomes in-plane polarization to the long axis. In the case of in-plane polarization to the long axis, ensemble EM near-field averages the maximum number of hotsites, and consequently, the SERS and SEF intensities are enhanced. On the other hand, in the case of orthogonal polarization (160° and 20° polarization, as shown in FIG. 6C and FIG. 8A), the gold nanoassembly induced low enhancement in the SERS and SEF emission.

Thus, the foregoing discussion discloses and describes merely exemplary embodiments of the present invention. As will be understood by those skilled in the art, the present invention may be embodied in other specific forms without departing from the spirit or essential characteristics thereof. Accordingly, the disclosure of the present invention is intended to be illustrative, but not limiting of the scope of the invention, as well as other claims. The disclosure, including any readily discernible variants of the teachings herein, defines, in part, the scope of the foregoing claim terminology such that no inventive subject matter is dedicated to the public.

The invention claimed is:
1. A polarization dependent surface enhanced Raman scattering system, comprising:
   a surface enhanced Raman scattering (SERS) active nanoassembly, comprising:
      a glass layer; and
      gold nanoparticles immobilized on the glass layer;
      wherein the gold nanoparticles are anisotropically assembled as a monolayer double row having a long axis, and wherein the gold nanoparticles have a spherical morphology,
   wherein an analyte is adsorbed onto the surface enhanced Raman scattering (SERS) active nanoassembly;
   a laser radiation source;
   an objective lens;
   a wave plate; and
   a detector;
   wherein the laser radiation source is disposed above the wave plate which is disposed above the SERS active nanoassembly which is disposed above the objective lens which is disposed above the detector, wherein the laser radiation source provides incident radiation on the analyte and the detector is positioned to receive scattered radiation from the analyte; and wherein the analyte is detected by the scattered radiation.

2. The polarization dependent surface enhanced Raman scattering system of claim 1, wherein the laser radiation source is a krypton ion laser that provides incident radiation having a wavelength of 400-800 nm or a helium-neon gas laser that provides incident radiation having a wavelength of 500-650 nm.

3. The polarization dependent surface enhanced Raman scattering system of claim 1, wherein the detector is a multichannel charge coupled device (CCD).

* * * * *